US009892477B2

(12) United States Patent
Barday

(10) Patent No.: US 9,892,477 B2
(45) Date of Patent: *Feb. 13, 2018

(54) DATA PROCESSING SYSTEMS AND METHODS FOR IMPLEMENTING AUDIT SCHEDULES FOR PRIVACY CAMPAIGNS

(71) Applicant: OneTrust, LLC, Atlanta, GA (US)

(72) Inventor: Kabir A. Barday, Atlanta, GA (US)

(73) Assignee: OneTrust, LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/633,703

(22) Filed: Jun. 26, 2017

(65) Prior Publication Data
US 2017/0293990 A1 Oct. 12, 2017

Related U.S. Application Data

(63) Continuation of application No. 15/256,419, filed on Sep. 2, 2016, now Pat. No. 9,691,090, which is a (Continued)

(51) Int. Cl.
G06Q 10/10 (2012.01)
G06Q 40/08 (2012.01)
(Continued)

(52) U.S. Cl.
CPC ....... *G06Q 50/265* (2013.01); *G06Q 10/0635* (2013.01); *G06Q 10/063114* (2013.01); (Continued)

(58) Field of Classification Search
CPC .......................... G06Q 30/0609; G06Q 50/265
(Continued)

(56) References Cited

U.S. PATENT DOCUMENTS 5,276,735 A 1/1994 Boebert et al.
6,816,944 B2 11/2004 Peng
(Continued)

FOREIGN PATENT DOCUMENTS

WO 2015116905 8/2015

OTHER PUBLICATIONS

International Search Report, dated Jun. 21, 2017, from corresponding International Application No. PCT/US2017/025600.
(Continued)

*Primary Examiner* — Jonathan P Ouellette
(74) *Attorney, Agent, or Firm* — Brient Globerman, LLC

(57) ABSTRACT

Data processing systems and methods for retrieving data regarding a plurality of data privacy campaigns and for using that data to assess a relative risk associated with the data privacy campaign. In various embodiments, the system may be adapted to: (1) display one or more visual summaries of one or more data flow diagrams that visually depicts key features of the data flow, such as whether data is confidential and/or encrypted; (2) allow for multiple users to be assigned responsibility for populating different respective questions that are required to define the data flow; (3) automatically assess and display a relative risk associated with each campaign; and (4) automatically set, monitor, and facilitate the timely completion of an audit schedule for each campaign.

30 Claims, 17 Drawing Sheets

Related U.S. Application Data continuation of application No. 15/169,643, filed on May 31, 2016.

(60) Provisional application No. 62/317,457, filed on Apr. 1, 2016.

(51) Int. Cl.
  *G06F 21/31* (2013.01)
  *G06Q 50/26* (2012.01)
  *G06Q 10/06* (2012.01)
  *G06Q 30/00* (2012.01)
  *G06F 21/62* (2013.01)

(52) U.S. Cl.
  CPC ... *G06Q 10/063116* (2013.01); *G06Q 30/018* (2013.01); *G06F 21/6245* (2013.01)

(58) Field of Classification Search
  USPC .................................................. 705/1.1–912
  See application file for complete search history.

(56) References Cited

U.S. PATENT DOCUMENTS

| | | | |
|---|---|---|---|
| 6,925,443 B1 | 8/2005 | Baggett, Jr. et al. | |
| 7,234,065 B2 | 6/2007 | Breslin et al. | |
| 7,251,624 B1 | 7/2007 | Lee et al. | |
| 7,260,830 B2 | 8/2007 | Sugimoto | |
| 7,287,280 B2 | 10/2007 | Young | |
| 7,478,157 B2 | 1/2009 | Bohrer et al. | |
| 7,603,356 B2 | 10/2009 | Schran et al. | |
| 7,729,940 B2 | 6/2010 | Harvey et al. | |
| 7,788,632 B2 | 8/2010 | Kuester et al. | |
| 7,801,758 B2 | 9/2010 | Gracie et al. | |
| 7,853,468 B2 | 12/2010 | Callahan et al. | |
| 7,877,812 B2 | 1/2011 | Koved et al. | |
| 7,885,841 B2 | 2/2011 | King | |
| 7,966,663 B2 | 6/2011 | Strickland et al. | |
| 7,991,559 B2 | 8/2011 | Dzekunov et al. | |
| 8,019,881 B2 | 9/2011 | Sandhu et al. | |
| 8,146,074 B2 | 3/2012 | Ito et al. | |
| 8,156,158 B2 | 4/2012 | Rolls et al. | |
| 8,176,334 B2 | 5/2012 | Vainstein | |
| 8,504,481 B2 * | 8/2013 | Motahari | G06F 21/577 705/51 |
| 8,578,036 B1 | 11/2013 | Holfelder et al. | |
| 8,583,694 B2 | 11/2013 | Siegel et al. | |
| 8,601,591 B2 | 12/2013 | Krishnamurthy et al. | |
| 8,612,420 B2 | 12/2013 | Sun et al. | |
| 8,612,993 B2 | 12/2013 | Grant et al. | |
| 8,683,502 B2 | 3/2014 | Shkedi et al. | |
| 8,712,813 B2 | 4/2014 | King | |
| 8,805,707 B2 | 8/2014 | Schumann, Jr. et al. | |
| 8,805,925 B2 | 8/2014 | Price et al. | |
| 8,812,342 B2 | 8/2014 | Barcelo et al. | |
| 8,819,253 B2 | 8/2014 | Simeloff et al. | |
| 8,826,446 B1 | 9/2014 | Liu et al. | |
| 8,914,299 B2 | 12/2014 | Pesci-Anderson et al. | |
| 8,943,076 B2 | 1/2015 | Stewart et al. | |
| 9,092,796 B2 | 7/2015 | Eversoll et al. | |
| 9,094,434 B2 | 7/2015 | Williams et al. | |
| 9,152,820 B1 | 10/2015 | Pauley, Jr. et al. | |
| 9,158,655 B2 | 10/2015 | Wadhwani et al. | |
| 9,172,706 B2 | 10/2015 | Krishnamurthy et al. | |
| 9,202,085 B2 | 12/2015 | Mawdsley et al. | |
| 9,215,252 B2 | 12/2015 | Smith et al. | |
| 9,288,118 B1 | 3/2016 | Pattan | |
| 9,338,188 B1 | 5/2016 | Ahn | |
| 9,348,802 B2 | 5/2016 | Massand | |
| 9,384,357 B2 | 7/2016 | Patil et al. | |
| 9,401,900 B2 | 7/2016 | Levasseur et al. | |
| 9,424,021 B2 | 8/2016 | Zamir | |
| 9,507,960 B2 | 11/2016 | Bell et al. | |
| 9,521,166 B2 | 12/2016 | Wilson | |
| 9,602,529 B2 | 3/2017 | Jones et al. | |
| 9,646,095 B1 | 5/2017 | Gottlieb et al. | |
| 9,652,314 B2 | 5/2017 | Mahiddini | |
| 9,654,541 B1 | 5/2017 | Kapczynski et al. | |
| 9,691,090 B1 | 6/2017 | Barday | |
| 9,721,108 B2 | 8/2017 | Krishnamurthy et al. | |
| 2002/0161594 A1 | 10/2002 | Bryan et al. | |
| 2003/0041250 A1 * | 2/2003 | Proudler | G06F 21/57 713/182 |
| 2004/0098285 A1 * | 5/2004 | Breslin | G06Q 10/10 713/193 |
| 2006/0075122 A1 | 4/2006 | Lindskog et al. | |
| 2007/0027715 A1 | 2/2007 | Gropper et al. | |
| 2007/0157311 A1 | 7/2007 | Meier et al. | |
| 2007/0266420 A1 | 11/2007 | Hawkins et al. | |
| 2007/0283171 A1 | 12/2007 | Breslin et al. | |
| 2008/0028435 A1 | 1/2008 | Strickland et al. | |
| 2009/0204452 A1 | 8/2009 | Iskandar et al. | |
| 2010/0121773 A1 | 5/2010 | Currier et al. | |
| 2010/0333012 A1 | 12/2010 | Adachi et al. | |
| 2011/0010202 A1 | 1/2011 | Neale | |
| 2011/0307957 A1 * | 12/2011 | Barcelo | G06F 21/552 726/25 |
| 2012/0102543 A1 | 4/2012 | Kohli et al. | |
| 2012/0116923 A1 | 5/2012 | Irving et al. | |
| 2012/0259752 A1 | 10/2012 | Agee | |
| 2013/0036110 A1 * | 2/2013 | Scott | G06F 17/30 707/722 |
| 2013/0218829 A1 | 8/2013 | Martinez | |
| 2013/0311224 A1 | 11/2013 | Heroux et al. | |
| 2013/0332362 A1 * | 12/2013 | Ciurea | G06Q 20/383 705/44 |
| 2013/0340086 A1 | 12/2013 | Blom | |
| 2014/0006616 A1 | 1/2014 | Aad et al. | |
| 2014/0012833 A1 | 1/2014 | Humprecht | |
| 2014/0032265 A1 | 1/2014 | Paprocki | |
| 2014/0040134 A1 * | 2/2014 | Ciurea | G06Q 20/383 705/44 |
| 2014/0047551 A1 | 2/2014 | Nagasundaram et al. | |
| 2014/0089039 A1 | 3/2014 | McClellan | |
| 2014/0208418 A1 | 7/2014 | Libin | |
| 2014/0278663 A1 | 9/2014 | Samuel et al. | |
| 2014/0283027 A1 | 9/2014 | Orona et al. | |
| 2014/0337466 A1 | 11/2014 | Li et al. | |
| 2015/0066577 A1 | 3/2015 | Christiansen et al. | |
| 2015/0106948 A1 | 4/2015 | Holman et al. | |
| 2015/0106949 A1 | 4/2015 | Holman et al. | |
| 2015/0169318 A1 | 6/2015 | Nash | |
| 2015/0229664 A1 | 8/2015 | Hawthorn et al. | |
| 2015/0242778 A1 | 8/2015 | Wilcox et al. | |
| 2015/0269384 A1 | 9/2015 | Holman et al. | |
| 2015/0356362 A1 | 12/2015 | Demos | |
| 2016/0048700 A1 | 2/2016 | Stransky-Heilkron | |
| 2016/0099963 A1 | 4/2016 | Mahaffey et al. | |
| 2016/0162269 A1 | 6/2016 | Pogorelik et al. | |
| 2016/0234319 A1 | 8/2016 | Griffin | |
| 2016/0321748 A1 | 11/2016 | Mahatma et al. | |
| 2016/0364736 A1 | 12/2016 | Maugans, III | |
| 2017/0142158 A1 | 5/2017 | Laoutaris et al. | |
| 2017/0161520 A1 | 6/2017 | Lockhart, III | |
| 2017/0177324 A1 | 6/2017 | Frank et al. | |
| 2017/0193624 A1 | 7/2017 | Tsai | |
| 2017/0206707 A1 | 7/2017 | Guay et al. | |
| 2017/0270318 A1 * | 9/2017 | Ritchie | G06Q 40/025 |
| 2017/0330197 A1 * | 11/2017 | DiMaggio | G06Q 30/018 |

OTHER PUBLICATIONS

International Search Report, dated Jun. 6, 2017, from corresponding International Application No. PCT/US2017/025605.

International Search Report, dated Jun. 6, 2017, from corresponding International Application No. PCT/US2017/025611.

Notice of Allowance, dated Apr. 12, 2017, from corresponding U.S. Appl. No. 15/256,419.

Notice of Allowance, dated May 5, 2017, from corresponding U.S. Appl. No. 15/254,901.

Office Action, dated Dec. 15, 2016, from corresponding U.S. Appl. No. 15/256,419.

(56) References Cited

OTHER PUBLICATIONS

Restriction Requirement, dated Jan. 18, 2017, from corresponding U.S. Appl. No. 15/256,430.
Restriction Requirement, dated Nov. 21, 2016, from corresponding U.S. Appl. No. 15/254,901.
TRUSTe Announces General Availability of Assessment Manager for Enterprises to Streamline Data Privacy Management with Automation, PRNewswire, Mar. 4, 2015.
Written Opinion of the International Searching Authority, dated Jun. 6, 2017, from corresponding International Application No. PCT/US2017/025611.
Written Opinion of the International Searching Authority, dated Jun. 21, 2017, from corresponding International Application No. PCT/US2017/025600.
Written Opinion of the International Searching Authority, dated Jun. 6, 2017, from corresponding International Application No. PCT/US2017/025605.
www.truste.com (1), 200150207, Internet Archive Wayback Machine, www.archive.org,2_7_2015.
International Search Report, dated Oct. 3, 2017, from corresponding International Application No. PCT/US2017/036912.
Written Opinion of the International Searching Authority, dated Oct. 3, 2017, from corresponding International Application No. PCT/US2017/036912.
International Search Report, dated Oct. 12, 2017, from corresponding International Application No. PCT/US2017/036888.
Written Opinion of the International Searching Authority, dated Oct. 12, 2017, from corresponding International Application No. PCT/US2017/036888.
International Search Report, dated Oct. 20, 2017, from corresponding International Application No. PCT/US2017/036917.
Written Opinion of the International Searching Authority, dated Oct. 20, 2017, from corresponding International Application No. PCT/US2017/036917.
Office Action, dated Nov. 1, 2017, from corresponding U.S. Appl. No. 15/169,658.
Notice of Allowance, dated Nov. 7, 2017, from corresponding U.S. Appl. No. 15/671,073.
Ghiglieri, Marco et al.; Personal DLP for Facebook, 2014 IEEE International Conference on Pervasive Computing and Communication Workshops (Percom Workshops); IEEE; Mar. 24, 2014; pp. 629-634.
International Search Report, dated Aug. 15, 2017, from corresponding International Application No. PCT/US2017/036919.
International Search Report, dated Aug. 8, 2017, from corresponding International Application No. PCT/US2017/036889.
International Search Report, dated Aug. 8, 2017, from corresponding International Application No. PCT/US2017/036890.
International Search Report, dated Aug. 8, 2017, from corresponding International Application No. PCT/US2017/036893.
International Search Report, dated Aug. 8, 2017, from corresponding International Application No. PCT/US2017/036901.
International Search Report, dated Aug. 8, 2017, from corresponding International Application No. PCT/US2017/036913.
International Search Report, dated Aug. 8, 2017, from corresponding International Application No. PCT/US2017/036920.
Invitation to Pay Additional Search Fees, dated Aug. 10, 2017, from corresponding International Application No. PCT/US2017/036912.
Invitation to Pay Additional Search Fees, dated Aug. 10, 2017, from corresponding International Application No. PCT/US2017/036917.
Korba, Larry et al.; "Private Data Discovery for Privacy Compliance in Collaborative Environments"; Cooperative Design, Visualization, and Engineering; Springer Berlin Heidelberg; Sep. 21, 2008; pp. 142-150.
Notice of Allowance, dated Aug. 18, 2017, from corresponding U.S. Appl. No. 15/619,455.
Office Action, dated Aug. 23, 2017, from corresponding U.S. Appl. No. 15/626,052.
Office Action, dated Jul. 21, 2017, from corresponding U.S. Appl. No. 15/256,430.
Restriction Requirement, dated Jul. 28, 2017, from corresponding U.S. Appl. No. 15/169,658.
Symantec, Symantex Data Loss Prevention—Discover, monitor, and protect confidential data; 2008; Symantec Corporation; http://www.mssuk.com/images/Symantec%2014552315_IRC_BR_DLP_03.09_sngl.pdf.
Written Opinion of the International Searching Authority, dated Aug. 15, 2017, from corresponding International Application No. PCT/US2017/036919.
Written Opinion of the International Searching Authority, dated Aug. 8, 2017, from corresponding International Application No. PCT/US2017/036889.
Written Opinion of the International Searching Authority, dated Aug. 8, 2017, from corresponding International Application No. PCT/US2017/036890.
Written Opinion of the International Searching Authority, dated Aug. 8, 2017, from corresponding International Application No. PCT/US2017/036893.
Written Opinion of the International Searching Authority, dated Aug. 8, 2017, from corresponding International Application No. PCT/US2017/036901.
Written Opinion of the International Searching Authority, dated Aug. 8, 2017, from corresponding International Application No. PCT/US2017/036913.
Written Opinion of the International Searching Authority, dated Aug. 8, 2017, from corresponding International Application No. PCT/US2017/036920.
Office Action, dated Aug. 24, 2017, from corresponding U.S. Appl. No. 15/619,451.
International Search Report, dated Aug. 21, 2017, from corresponding International Application No. PCT/US2017/036914.
Invitation to Pay Additional Search Fees, dated Aug. 24, 2017, from corresponding International Application No. PCT/US2017/036888.
Office Action, dated Aug. 24, 2017, from corresponding U.S. Appl. No. 15/169,643.
Office Action, dated Aug. 29, 2017, from corresponding U.S. Appl. No. 15/619,237.
Written Opinion of the International Searching Authority, dated Aug. 21, 2017, from corresponding International Application No. PCT/US2017/036914.
Office Action, dated Aug. 30, 2017, from corresponding U.S. Appl. No. 15/619,212.
Office Action, dated Aug. 30, 2017, from corresponding U.S. Appl. No. 15/619,382.
Office Action, dated Sep. 1, 2017, from corresponding U.S. Appl. No. 15/619,459.
International Search Report, dated Aug. 29, 2017, from corresponding International Application No. PCT/US2017/036898.
International Search Report, dated Sep. 1, 2017, from corresponding International Application No. PCT/US2017/036896.
Office Action, dated Sep. 11, 2017, from corresponding U.S. Appl. No. 15/619,375.
Office Action, dated Sep. 11, 2017, from corresponding U.S. Appl. No. 15/619,478.
Office Action, dated Sep. 19, 2017, from corresponding U.S. Appl. No. 15/671,073.
Office Action, dated Sep. 5, 2017, from corresponding U.S. Appl. No. 15/619,469.
Office Action, dated Sep. 6, 2017, from corresponding U.S. Appl. No. 15/619,479.
Office Action, dated Sep. 8, 2017, from corresponding U.S. Appl. No. 15/619,251.
Written Opinion of the International Searching Authority, dated Aug. 29, 2017, from corresponding International Application No. PCT/US2017/036898.
Written Opinion of the International Searching Authority, dated Sep. 1, 2017, from corresponding International Application No. PCT/US2017/036896.
Office Action, dated Sep. 22, 2017, from corresponding U.S. Appl. No. 15/619,278.
Notice of Allowance, dated Sep. 27, 2017, from corresponding U.S. Appl. No. 15/626,052.

(56) References Cited

OTHER PUBLICATIONS

Final Office Action, dated Nov. 29, 2017, from corresponding U.S. Appl. No. 15/619,237.
Notice of Allowance, dated Dec. 6, 2017, from corresponding U.S. Appl. No. 15/619,451.
Notice of Allowance, dated Dec. 6, 2017, from corresponding U.S. Appl. No. 15/619,459.
Notice of Allowance, dated Dec. 12, 2017, from corresponding U.S. Appl. No. 15/169,643.
Notice of Allowance, dated Dec. 12, 2017, from corresponding U.S. Appl. No. 15/619,212.
Notice of Allowance, dated Dec. 12, 2017, from corresponding U.S. Appl. No. 15/619,382.

* cited by examiner

Edit data flow: Internet Usage History — 1700

Data Flow Info

Data Flow Name*: Internet Usage History

Description: Data flow involved with tracking internet usage.

Business Group: Internet

Business Rep: Me | Someone Else | Jeff Hill (jeffhill@acme.com)

Data Collection

| Contact Info | Financial/Billing Info | Online Identifiers | Personal Details |
|---|---|---|---|
| ☐ Account Holder Name | ☐ Credit Card Num | ☑ IP Address | ☐ Birthdate |
| ☐ Other Individual Name | ☐ Billing Address | ☐ Device Type | ☐ Credit Score |

Save Changes    Cancel

FIG. 17

DATA PROCESSING SYSTEMS AND METHODS FOR IMPLEMENTING AUDIT SCHEDULES FOR PRIVACY CAMPAIGNS

CROSS REFERENCE TO RELATED APPLICATIONS

This application is a continuation of U.S. patent application Ser. No. 15/256,419, entitled "Data Processing Systems and Methods for Operationalizing Privacy Compliance and Assessing the Risk of Various Respective Privacy Campaigns," filed Sep. 2, 2016, which is a continuation of U.S. patent application Ser. No. 15/169,643, entitled "Data Processing Systems and Methods for Operationalizing Privacy Compliance and Assessing the Risk of Various Respective Privacy Campaigns", filed May 31, 2016, which claims the benefit of U.S. Provisional Application No. 62/317,457, entitled "Data Processing Systems and Methods for Operationalizing Privacy Compliance and Assessing the Risk of Various Respective Privacy Campaigns," filed Apr. 1, 2016, all of which are incorporated herein by reference in their entirety.

TECHNICAL FIELD

This disclosure relates to a data processing system and methods for retrieving data regarding a plurality of privacy campaigns, and for using that data to assess a relative risk associated with the data privacy campaign, provide an audit schedule for each campaign, and electronically display campaign information.

BACKGROUND

Over the past years, privacy and security policies, and related operations have become increasingly important. Breaches in security, leading to the unauthorized access of personal data (which may include sensitive personal data) have become more frequent among companies and other organizations of all sizes. Such personal data may include, but is not limited to, personally identifiable information (PII), which may be information that directly (or indirectly) identifies an individual or entity. Examples of PII include names, addresses, dates of birth, social security numbers, and biometric identifiers such as a person's fingerprints or picture. Other personal data may include, for example, customers' Internet browsing habits, purchase history, or even their preferences (i.e., likes and dislikes, as provided or obtained through social media). While not all personal data may be sensitive, in the wrong hands, this kind of information may have a negative impact on the individuals or entities whose sensitive personal data is collected, including identity theft and embarrassment. Not only would this breach have the potential of exposing individuals to malicious wrongdoing, the fallout from such breaches may result in damage to reputation, potential liability, and costly remedial action for the organizations that collected the information and that were under an obligation to maintain its confidentiality and security. These breaches may result in not only financial loss, but loss of credibility, confidence, and trust from individuals, stakeholders, and the public.

Many organizations that obtain, use, and transfer personal data, including sensitive personal data, have begun to address these privacy and security issues. To manage personal data, many companies have attempted to implement operational policies and processes that comply with legal requirements, such as Canada's Personal Information Protection and Electronic Documents Act (PIPEDA) or the U.S.'s Health Insurance Portability and Accountability Act (HIPPA) protecting a patient's medical information. The European Union's General Data Protection Regulation (GDPR) can fine companies up to 4% of their global worldwide turnover (revenue) for not complying with its regulations (companies must comply by March 2018). These operational policies and processes also strive to comply with industry best practices (e.g., the Digital Advertising Alliance's Self-Regulatory Principles for Online Behavioral Advertising). Many regulators recommend conducting privacy impact assessments, or data protection risk assessments along with data inventory mapping. For example, the GDPR requires data protection impact assessments. Additionally, the United Kingdom ICO's office provides guidance around privacy impact assessments. The OPC in Canada recommends personal information inventory, and the Singapore PDPA specifically mentions personal data inventory mapping.

Thus, developing operational policies and processes may reassure not only regulators, but also an organization's customers, vendors, and other business partners.

For many companies handling personal data, privacy audits, whether done according to AICPA Generally Accepted Privacy Principles, or ISACA's IT Standards, Guidelines, and Tools and Techniques for Audit Assurance and Control Professionals, are not just a best practice, they are a requirement (for example, Facebook and Google will be required to perform 10 privacy audits each until 2032 to ensure that their treatment of personal data comports with the expectations of the Federal Trade Commission). When the time comes to perform a privacy audit, be it a compliance audit or adequacy audit, the lack of transparency or clarity into where personal data comes from, where is it stored, who is using it, where it has been transferred, and for what purpose is it being used, may bog down any privacy audit process. Even worse, after a breach occurs and is discovered, many organizations are unable to even identify a clear-cut organizational owner responsible for the breach recovery, or provide sufficient evidence that privacy policies and regulations were complied with.

In light of the above, there is currently a need for improved systems and methods for monitoring compliance with corporate privacy policies and applicable privacy laws.

SUMMARY

According to exemplary embodiments, a system for operationalizing privacy compliance is described herein. The system may be comprised of one or more servers and client computing devices that execute one or more software modules that perform functions and methods related to the input, processing, storage, retrieval, and display of campaign data related to a privacy campaign. A privacy campaign may be any business function, system, product, technology, process, project, engagement, initiative, campaign, etc., that may utilize personal data collected from one or more persons or entities. Campaign data may data representative of one or more attributes related to the personal data collected as part of the campaign.

A computer-implemented data processing system and method is operable for electronically receiving the input of campaign data associated with a privacy campaign, and electronically calculating a risk level for the privacy campaign based on the campaign data.

The system is operable for displaying on a graphical user interface (GUI) a prompt to create an electronic record for a privacy campaign. The system receives a command to create an electronic record for the privacy campaign, creates an electronic record for the privacy campaign and digitally stores the record. The system presents on one or more graphical user interfaces a plurality of prompts for the input of campaign data related to the privacy campaign. It electronically receives any campaign data input by one or more users. The privacy campaign data may relate to a description of the campaign, one or more types of personal data related to the campaign, a subject from which the personal data was collected, the storage of the personal data, and access to the personal data.

The system processes the campaign data by electronically associating the campaign data with the record for the privacy campaign, and digitally storing the campaign data associated with the record for the campaign.

Using a microprocessor, the system calculates a "Risk Level" for the campaign based on the campaign data, electronically associates the risk level with the record for the campaign; and digitally stores the risk level associated with the record for the campaign (e.g., in a storage device such as a networked hard drive, a cloud drive, the hard drive of one or more computing devices, etc.).

The users of the system may be an owner of the campaign, who may be a privacy officer (i.e., personnel working in an organization under the Chief Privacy Officer). The privacy officer may input an initial portion of the campaign data, such as the name of the campaign, the description of the campaign, and the business group responsible for administering the privacy operations related to that campaign.

The system is also operable for accepting an input to add one or more collaborators designated by one or more users (who may be an owner) to input campaign data. Once a user designates a collaborator, who may be another owner or a business office representative, the system sends an electronic message to the collaborator regarding the addition of the collaborator for adding campaign data for the privacy campaign (e.g., letting the collaborator know that he has been added to the campaign, providing him with system login details, responsibilities, and deadlines for providing his portion of the campaign data). The collaborator may be designated to input different portions of the campaign data. The collaborator may be designated to provide input for one or more prompts, including one or more questions. The collaborator may be designated to provide input for part of a question.

The system is operable for accepting one or more inputs of campaign data from the users, who may be owners or collaborator(s), and for any campaign data that has been added, the system electronically associates the campaign data received from the input of the users with the record of the campaign, and digitally stores the campaign data received from the input of the collaborator with the record for the campaign (again, this may also be in a storage device such as a networked hard drive, a cloud drive, the hard drive of one or more computing devices, etc.).

The system can collect this campaign data by presenting a plurality of prompts for inputting the campaign data to the users (who may be a privacy officer, a business rep, or other collaborators). The prompts may be presented through a series of computer-generated GUIs (for example, webpages), wherein each GUI displays one or more of the prompts for campaign data, and wherein each GUI page is presented one at a time (e.g., in a screen by screen manner, for example, in five phases as shown in FIGS. 8 through 14). One or more graphical user interface pages may be an online form comprising one or more fields in which a user can input data. The graphical user interface may have a visually displayed shape (such as a circle) that can be filled by the user to input data. The graphical user interface may have a drop-down menu from which a user can select an item.

Also, to facilitate collaboration, a computer implemented method may be operable for instantiating a real-time communication session overlaying a portion of a user interface. One or more GUI pages having prompts may display an indicator (e.g., the "comment button" shown in FIGS. 9 through 13), wherein if the indicator is selected, it retrieves a list of one or more collaborators associated with at least one record related to the information displayed on the online graphical user interface, wherein the list of collaborators includes the user and at least one other person. The system then electronically instantiates a real-time communication session (e.g., an instant messaging session, a chat session, etc.) between the user and the one or more collaborators in a computer-generated window, wherein the window having the real-time communications session overlays the online graphical user interface, covering at least a portion of the graphical user interface.

When the user responds to the prompts and enters inputs (for example, through fields, drop down menus, check boxes, radial selections), the system may be operable to automatically populate one or more fields based on the data input history of the user. The system may also be operable to automatically populate one or more fields for the entry of data inputs based on the type of campaign data entered from a previous input (e.g., if the input is related to personal data, the check boxes commonly used for personal data can be automatically checked. See, e.g., FIG. 10). Based on the input of campaign data received from the one or more users, the system can present further prompts related to the campaign data that was input (e.g., if a user selects a box that indicates that the personal information being collected includes personal data, the user can be presented with another dialog with more selections related to personal data. See, e.g., FIG. 10).

The system is also operable for sending reminders. If required campaign data has not been received, the system sends one or more electronic notifications that indicates that required campaign data has not yet been provided, thereby facilitating the gathering of different portions of information from one or more collaborators until all the required campaign data for a privacy campaign has been input.

The system is operable to use the campaign data input into the system to calculate a "Risk Level". The system electronically retrieves from a database the campaign data associated with the record for the campaign, electronically determines a plurality of "weighting factors" for the campaign, wherein the plurality of weighting factors are based upon a number of factors including the nature of the personal data associated with the campaign, the physical location of the personal data associated with the campaign, the number of individuals having access to the personal data associated with the campaign, the length of time that the personal data associated with the campaign will be retained in storage, the type of individual from which the personal data associated with the campaign originated, and the country of residence of the individual from which the personal data associated with the campaign originated. Each weighting factor is electronically assigned a higher numerical value if the risk associated with the factor is higher.

In addition to the determining the weighting factors, the system electronically assigns a "relative risk rating" for each of the plurality of factors. Based on weighting factors and the relative risk rating for each of the plurality of factors, the system electronically calculates a risk level for the campaign. The system may use an algorithm to make this calculation, for example, the Risk Level may be electronically calculated as the sum of a plurality of: a weighting factor multiplied by the relative risk rating of the factor (i.e., Risk Level for campaign=(Weighting Factor of Factor 1)*(Relative Risk Rating of Factor 1)+(Weighting Factor of Factor 2)*(Relative Risk Rating of Factor 2)+ . . . (Weighting Factor of Factor N)*(Relative Risk Rating of Factor N).

The system may also determine an Overall Risk Assessment for the campaign and digitally store the Overall Risk Assessment with the record for the campaign, and wherein the Overall Risk Assessment is determined based upon a plurality of numerical ranges of risk levels (e.g., a campaign having a Risk Level of 1-7 is "low risk," (2) campaigns with a Risk Level of 8-15 are "medium risk," and (3) campaigns with a Risk Level of over 16 as "high risk").

The system may also be operable to electronically retrieve the campaign record and the campaign data associated with the record, and generating for display a computer-generated user interface comprising an inventory page (e.g., the inventory page shown in FIG. 15). The inventory page may display a list of a plurality of campaigns, and visual indicators that relate to the risk level for each listed campaign. The visual indicators may represent an overall risk assessment for the campaign. The visual indicators may be an upward pointing arrow, a downward pointing arrow, or different colors for each overall risk assessment level. On the inventory page, the plurality of campaigns can be sorted based on risk.

The system, when displaying any information, including information on the inventory page, can display information based on the permissions assigned to each user. The system may receive a login from the user, and based upon the identity of the user, determining which campaign-related data the one or more users is authorized to view. The system retrieves and displays only the campaign data that the user is authorized to view (for example, on the inventory page, a user that is a business rep may not be able to see every campaign, but only the campaigns that he or she is assigned to).

A computer-implemented data processing system and method is operable for assigning a schedule for a privacy audit associated with a privacy campaign. The system is operable for displaying on a graphical user interface a prompt to create an electronic record for a privacy campaign, receiving a command to create an electronic record for the privacy campaign, creating an electronic record for the privacy campaign and digitally storing the record, presenting on one or more graphical user interfaces a plurality of prompts for the input of campaign data related to the privacy campaign, and electronically receiving campaign data input by one or more users. The campaign data may relate to a description of the campaign, one or more types of personal data related to the campaign, a subject from which the personal data was collected, the storage of the personal data, and access to the personal data. The system processes the campaign data by electronically associating the campaign data with the record for the privacy campaign, digitally storing the campaign data associated with the record for the campaign, and assigning a privacy audit schedule for the campaign based on the risk associated with the campaign (which may be the risk level for the campaign, or the overall risk assessment for the campaign), wherein the audit schedule comprises a timeframe until the scheduled privacy audit. The audit schedule may be a default audit schedule predetermined for the risk associated with the campaign. The default audit schedule, which can be modifiable, may be based on privacy laws, company policies, or the like.

After the audit schedule for the campaign has been assigned, it may be modified. The system may be operable to receive an input to modify the audit schedule assigned to the campaign and determine whether the audit schedule assigned to the campaign is modifiable (e.g., modifiable by a user of the system). If the audit schedule assigned to the campaign is modifiable, the system modifies the audit schedule for the campaign. If the audit schedule is not modifiable, electronically displaying an indication that the audit schedule is not modifiable, a user can send a request to modify the audit schedule. The system receives the request to modify the audit schedule for the campaign, and may send an electronic message to persons having the authority to grant permission to modify the audit schedule, thereby letting them know that a request to modify the audit schedule is pending.

The system can determine whether a threshold amount of time until the privacy audit has been reached, and if the threshold has been reached, generate an electronic alert indicating that the privacy audit deadline is in the threshold amount of time (e.g., generating an alert that there is 90 days until the privacy audit deadline, if 90 days is one threshold). If the system receives an electronic confirmation that the scheduled privacy audit has been completed, it resets the audit schedule's timeframe until the next privacy audit. The electronic confirmation may be an electronic verification generated when all portions of the audit have been verified as completed by one or more collaborators. The system may further operable for receiving documentation related to the compliance of the privacy campaign, electronically associating the documentation received with the record of the campaign, and digitally storing the documentation associated with the record for the campaign in an electronic storage device (e.g., in a storage device such as a networked hard drive, a cloud drive, the hard drive of one or more computing devices, etc.).

The system may be operable to facilitate the auditing and compliance process by determining if the scheduled privacy audit is overdue based on whether an electronic confirmation that the scheduled privacy audit has been completed has been received. If the scheduled privacy audit is overdue, the system may generate an electronic alert indicating that the privacy audit is overdue.

The system can also display audit related information to the user by electronically retrieving the campaign record and the campaign data associated with the record (including audit information), and generating for display a computer-generated user interface comprising an inventory page, wherein the inventory page displays a list of a plurality of campaigns and audit information, which may be based upon the audit schedule, for one or more of the plurality of campaigns. The audit information displayed may show whether an audit associated with the campaign is pending, complete, or due, and indicate the number of days before the audit is to be conducted (see, e.g., FIG. 15).

A computer-implemented data processing method is operable for generating a data flow diagram for a privacy campaign. The system is operable for displaying on a graphical user interface a prompt to create an electronic record for a privacy campaign, receiving a command to create an electronic record for the privacy campaign, creating an electronic record for the privacy campaign and digitally storing the record, presenting on one or more graphical user interfaces a plurality of prompts for the input of campaign data, and electronically receiving campaign data input by one or more users. The campaign data may relate to a description of the campaign, one or more types of personal data related to the campaign, a subject from which the personal data was collected, the storage of the personal data, and access to the personal data. The system processes the campaign data by electronically associating the campaign data with the record for the privacy campaign, and generating for display a data flow diagram on a computer-generated graphical user interface, wherein the data flow diagram comprises indicators related to the accessibility and encryption of the personal data related to the campaign.

The data flow diagram may display a heading indicative of the source of the personal data, the storage destination of the personal data, and access related to the personal data. The system is operable to generate one or more on on-screen objects shown in the data flow diagram, wherein each object contains a hyperlink label indicative of the source of the personal data, the storage destination of the personal data, and access related to the personal data, wherein additional campaign data relating to the campaign data associated with the hyperlinked word is displayed if a cursor is moved over the hyperlink label (e.g., on FIG. 16, the objects are rectangular boxes, the boxes containing the hyperlinked text Customers, Internet Usage, Customer Support, and Billing System).

Based on the campaign data associated with the campaign, the system may determine whether the personal data related to each of the hyperlink labels is confidential. If the personal data is confidential, the system generates an indicator indicating that the data associated with the hyperlink label is confidential, such as an "open eye" icon as show in FIG. 16. The system may also generate for display information relating to whether the source of the personal data includes minors, and generate for display an indication of whether consent was given by the source of the personal data to use any sensitive information, as well as the manner in which the consent was given (e.g., through an end user license agreement EULA). The system may also display on the data flow diagram one or more parameters related to the backup and retention of the personal data in the storage destination of the personal data.

The system may also generate on the data flow diagram data flow lines having arrows to indicate the data flow of personal data from source, to storage destination, to which entities or applications have access. If the system determines whether any of the data associated with the source, stored in a storage destination, being used by an entity or application, or data flow of data flowing to one or more entities or systems associated with the campaign is designated as encrypted, it can generate indicators on the data flow diagram. The system may generate a locked lock icon to indicate encrypted data, and generate an unlocked lock icon to indicate unencrypted data. The system may generate a locked lock icon to indicate encrypted data flow, and may generate an unlocked lock icon to indicate unencrypted data flow. The data flow lines may be colored differently to indicate whether the data flow is encrypted or unencrypted, and those colors may be distinguishable by a viewer that suffers from color blindness.

BRIEF DESCRIPTION OF THE DRAWINGS

Various embodiments of a system and method for operationalizing privacy compliance and assessing risk of privacy campaigns are described below. In the course of this description, reference will be made to the accompanying drawings, which are not necessarily drawn to scale, and wherein:

FIG. 8 is an example of a Graphical User Interface (GUI) showing a dialog that allows for entry of description information related to a privacy campaign.

FIG. 9 shows example of a notification to a business representative (i.e., owner) related to his/her assignment of a privacy campaign.

FIG. 10 is an example of a GUI showing a dialog allowing entry of the type of personal data that is being collected for a privacy campaign.

FIG. 11 is an example of a GUI that shows a dialog that allows collection of campaign data regarding the subject from whom the personal data was collected.

FIG. 12 is an example of a GUI that shows a dialog for inputting information regarding where the personal data related to a campaign is stored.

FIG. 13 is an example of a GUI that shows information regarding the access of the personal data related to a campaign.

FIG. 14 is an example of an instant messaging session overlaid on top of a GUI, wherein the GUI contains prompts for the entry or selection of campaign data.

FIG. 17 is an example of a GUI showing a page that allows editing of campaign data.

DETAILED DESCRIPTION

Figure 1:
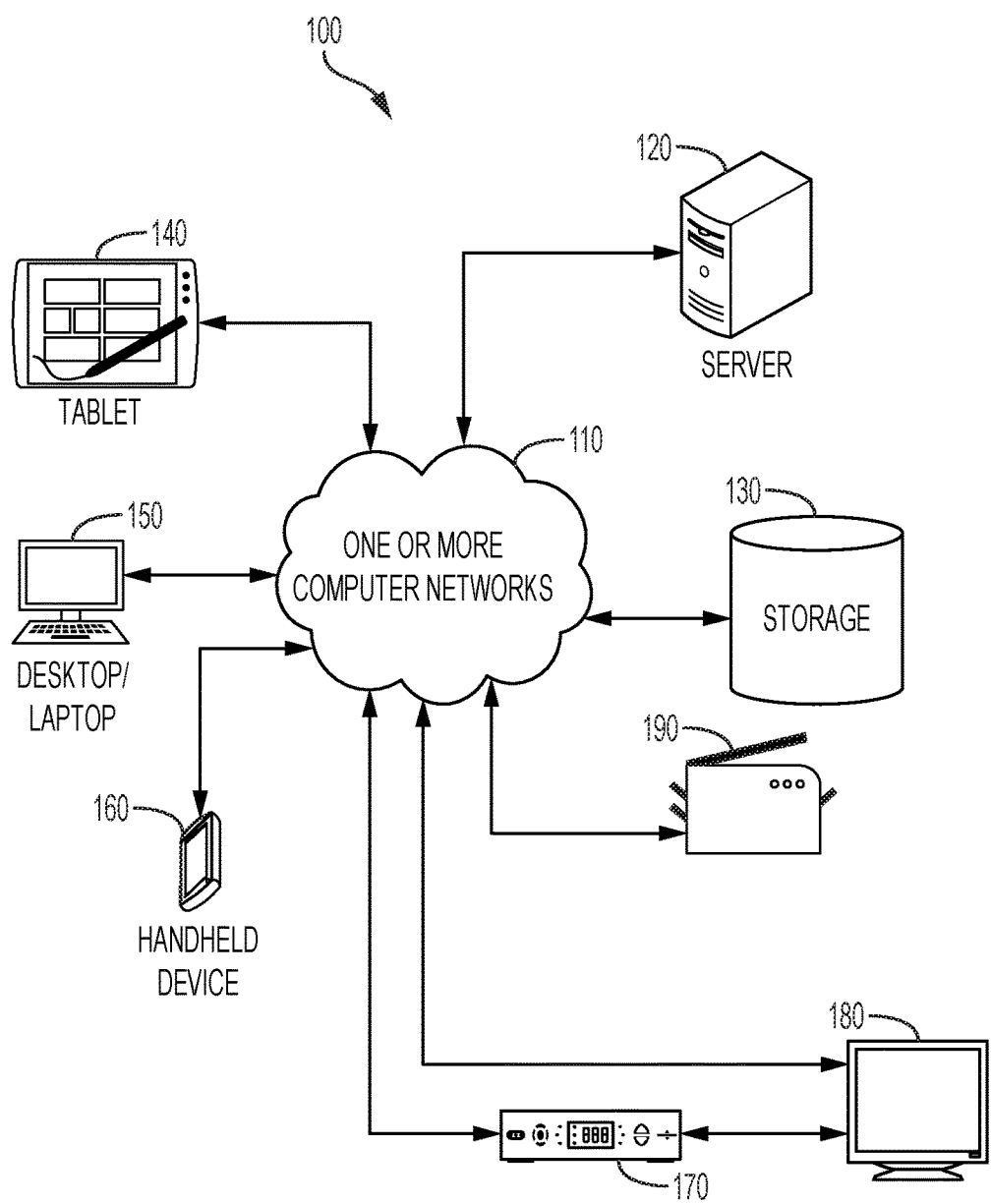
FIG. 1 is diagram illustrating an exemplary network environment in which the present system and methods for operationalizing privacy compliance may operate.

Various embodiments now will be described more fully hereinafter with reference to the accompanying drawings. It should be understood that the invention may be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Overview

According to exemplary embodiments, a system for operationalizing privacy compliance is described herein. The system may be comprised of one or more servers and client computing devices that execute software modules that facilitate various functions.

A Main Privacy Compliance Module is operable to allow a user to initiate the creation of a privacy campaign (i.e., a business function, system, product, technology, process, project, engagement, initiative, campaign, etc., that may utilize personal data collected from one or more persons or entities). The personal data may contain PII that may be sensitive personal data. The user can input information such as the name and description of the campaign. The user may also select whether he/she will take ownership of the campaign (i.e., be responsible for providing the information needed to create the campaign and oversee the conducting of privacy audits related to the campaign), or assign the campaign to one or more other persons. The Main Privacy Compliance Module can generate a sequence or serious of GUI windows that facilitate the entry of campaign data representative of attributes related to the privacy campaign (e.g., attributes that might relate to the description of the personal data, what personal data is collected, whom the data is collected from, the storage of the data, and access to that data).

Based on the information input, a Risk Assessment Module may be operable to take into account Weighting Factors and Relative Risk Ratings associated with the campaign in order to calculate a numerical Risk Level associated with the campaign, as well as an Overall Risk Assessment for the campaign (i.e., low-risk, medium risk, or high risk). The Risk Level may be indicative of the likelihood of a breach involving personal data related to the campaign being compromised (i.e., lost, stolen, accessed without authorization, inadvertently disclosed, maliciously disclosed, etc.). An inventory page can visually depict the Risk Level for one or more privacy campaigns.

After the Risk Assessment Module has determined a Risk Level for a campaign, a Privacy Audit Module may be operable to use the Risk Level to determine an audit schedule for the campaign. The audit schedule may be editable, and the Privacy Audit Module also facilitates the privacy audit process by sending alerts when a privacy audit is impending, or sending alerts when a privacy audit is overdue.

The system may also include a Data Flow Diagram Module for generating a data flow diagram associated with a campaign. An exemplary data flow diagram displays one or more shapes representing the source from which data associated with the campaign is derived, the destination (or location) of that data, and which departments or software systems may have access to the data. The Data Flow Diagram Module may also generate one or more security indicators for display. The indicators may include, for example, an "eye" icon to indicate that the data is confidential, a "lock" icon to indicate that the data, and/or a particular flow of data, is encrypted, or an "unlocked lock" icon to indicate that the data, and/or a particular flow of data, is not encrypted. Data flow lines may be colored differently to indicate whether the data flow is encrypted or unencrypted.

The system also provides for a Communications Module that facilitates the creation and transmission of notifications and alerts (e.g., via email). The Communications Module may also instantiate an instant messaging session and overlay the instant messaging session over one or more portions of a GUI in which a user is presented with prompts to enter or select information.

Exemplary Technical Platforms

As will be appreciated by one skilled in the relevant field, a system for operationalizing privacy compliance and assessing risk of privacy campaigns may be, for example, embodied as a computer system, a method, or a computer program product. Accordingly, various embodiments may take the form of an entirely hardware embodiment, an entirely software embodiment, or an embodiment combining software and hardware aspects. Furthermore, particular embodiments may take the form of a computer program product stored on a computer-readable storage medium having computer-readable instructions (e.g., software) embodied in the storage medium. Various embodiments may take the form of web, mobile, wearable computer-implemented, computer software. Any suitable computer-readable storage medium may be utilized including, for example, hard disks, compact disks, DVDs, optical storage devices, and/or magnetic storage devices.

Various embodiments are described below with reference to block diagrams and flowchart illustrations of methods, apparatuses (e.g., systems) and computer program products. It should be understood that each step of the block diagrams and flowchart illustrations, and combinations of steps in the block diagrams and flowchart illustrations, respectively, may be implemented by a computer executing computer program instructions. These computer program instructions may be loaded onto a general purpose computer, special purpose computer, or other programmable data processing apparatus to produce a machine, such that the instructions which execute on the computer or other programmable data processing apparatus to create means for implementing the functions specified in the flowchart step or steps These computer program instructions may also be stored in a computer-readable memory that may direct a computer or other programmable data processing apparatus to function in a particular manner such that the instructions stored in the computer-readable memory produce an article of manufacture that is configured for implementing the function specified in the flowchart step or steps. The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide steps for implementing the functions specified in the flowchart step or steps.

Accordingly, steps of the block diagrams and flowchart illustrations support combinations of mechanisms for performing the specified functions, combinations of steps for performing the specified functions, and program instructions for performing the specified functions. It should also be understood that each step of the block diagrams and flowchart illustrations, and combinations of steps in the block diagrams and flowchart illustrations, may be implemented by special purpose hardware-based computer systems that perform the specified functions or steps, or combinations of special purpose hardware and other hardware executing appropriate computer instructions.

Example System Architecture

FIG. 1 is a block diagram of a System 100 according to a particular embodiment. As may be understood from this figure, the System 100 includes one or more computer networks 110, a Server 120, a Storage Device 130 (which may contain one or more databases of information), one or more remote client computing devices such as a tablet computer 140, a desktop or laptop computer 150, or a handheld computing device 160, such as a cellular phone, browser and Internet capable set-top boxes 170 connected with a TV 180, or even smart TVs 180 having browser and Internet capability. The client computing devices attached to the network may also include copiers/printers 190 having hard drives (a security risk since copies/prints may be stored on these hard drives). The Server 120, client computing devices, and Storage Device 130 may be physically located in a central location, such as the headquarters of the organization, for example, or in separate facilities. The devices may be owned or maintained by employees, contractors, or other third parties (e.g., a cloud service provider). In particular embodiments, the one or more computer networks 115 facilitate communication between the Server 120, one or more client computing devices 140, 150, 160, 170, 180, 190, and Storage Device 130.

The one or more computer networks 115 may include any of a variety of types of wired or wireless computer networks such as the Internet, a private intranet, a public switched telephone network (PSTN), or any other type of network. The communication link between the Server 120, one or more client computing devices 140, 150, 160, 170, 180, 190, and Storage Device 130 may be, for example, implemented via a Local Area Network (LAN) or via the Internet.

Example Computer Architecture Used within the System

Figure 2:
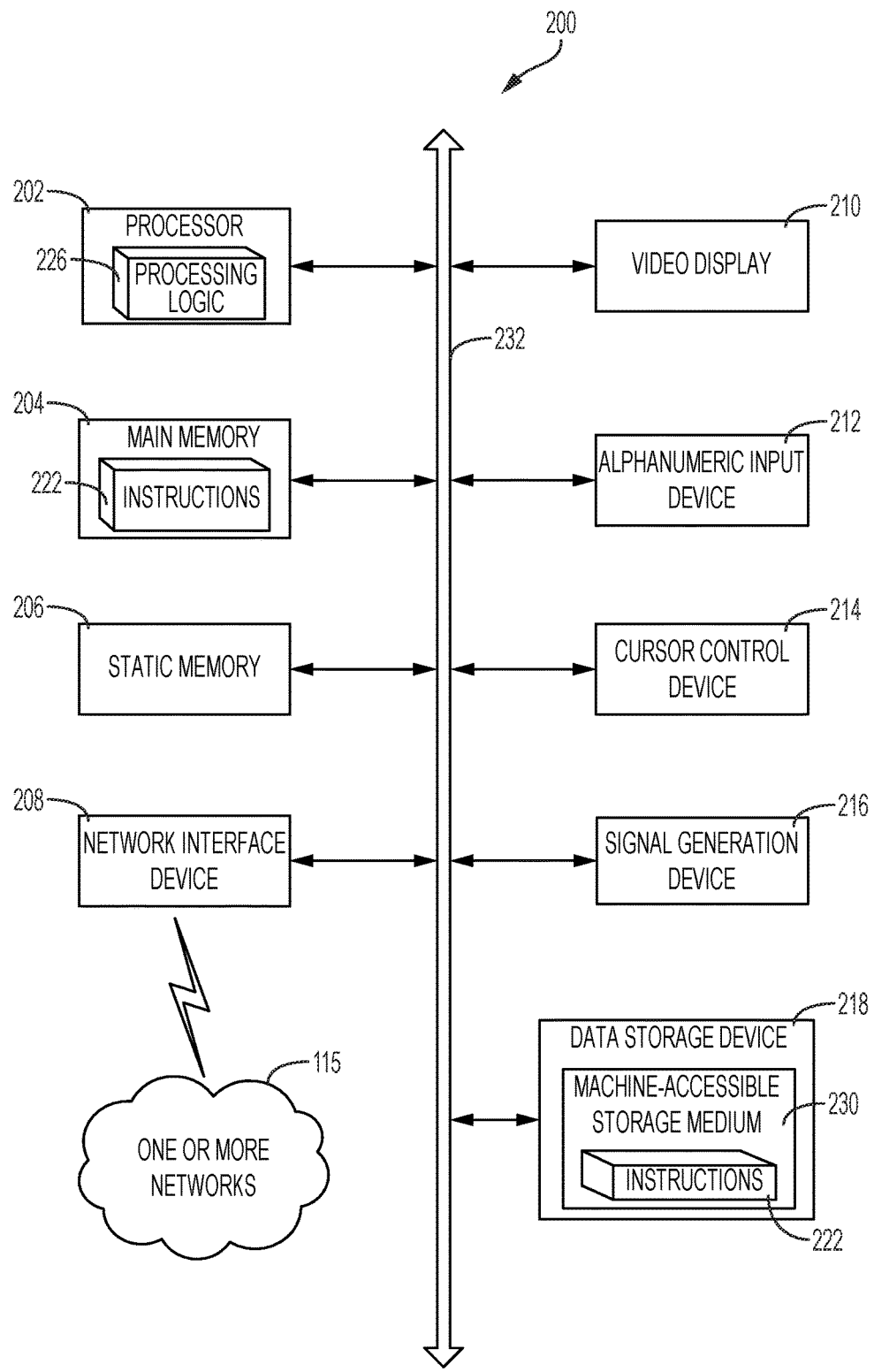
FIG. 2 is a schematic diagram of a computer (such as the server 120, or user device 140, 150, 160, 170, 180, 190) that is suitable for use in various embodiments.

FIG. 2 illustrates a diagrammatic representation of the architecture of a computer 200 that may be used within the System 100, for example, as a client computer (e.g., one of computing devices 140, 150, 160, 170, 180, 190, shown in FIG. 1), or as a server computer (e.g., Server 120 shown in FIG. 1). In exemplary embodiments, the computer 200 may be suitable for use as a computer within the context of the System 100 that is configured to operationalize privacy compliance and assess risk of privacy campaigns. In particular embodiments, the computer 200 may be connected (e.g., networked) to other computers in a LAN, an intranet, an extranet, and/or the Internet. As noted above, the computer 200 may operate in the capacity of a server or a client computer in a client-server network environment, or as a peer computer in a peer-to-peer (or distributed) network environment. The computer 200 may be a personal computer (PC), a tablet PC, a set-top box (STB), a Personal Digital Assistant (PDA), a cellular telephone, a web appliance, a server, a network router, a switch or bridge, or any other computer capable of executing a set of instructions (sequential or otherwise) that specify actions to be taken by that computer. Further, while only a single computer is illustrated, the term "computer" shall also be taken to include any collection of computers that individually or jointly execute a set (or multiple sets) of instructions to perform any one or more of the methodologies discussed herein.

An exemplary computer 200 includes a processing device 202, a main memory 204 (e.g., read-only memory (ROM), flash memory, dynamic random access memory (DRAM) such as synchronous DRAM (SDRAM) or Rambus DRAM (RDRAM), etc.), a static memory 206 (e.g., flash memory, static random access memory (SRAM), etc.), and a data storage device 218, which communicate with each other via a bus 232.

The processing device 202 represents one or more general-purpose processing devices such as a microprocessor, a central processing unit, or the like. More particularly, the processing device 202 may be a complex instruction set computing (CISC) microprocessor, reduced instruction set computing (RISC) microprocessor, very long instruction word (VLIW) microprocessor, or processor implementing other instruction sets, or processors implementing a combination of instruction sets. The processing device 202 may also be one or more special-purpose processing devices such as an application specific integrated circuit (ASIC), a field programmable gate array (FPGA), a digital signal processor (DSP), network processor, or the like. The processing device 202 may be configured to execute processing logic 226 for performing various operations and steps discussed herein.

The computer 200 may further include a network interface device 208. The computer 200 also may include a video display unit 210 (e.g., a liquid crystal display (LCD) or a cathode ray tube (CRT)), an alphanumeric input device 212 (e.g., a keyboard), a cursor control device 214 (e.g., a mouse), and a signal generation device 216 (e.g., a speaker). The data storage device 218 may include a non-transitory computer-readable storage medium 230 (also known as a non-transitory computer-readable storage medium or a non-transitory computer-readable medium) on which is stored one or more sets of instructions 222 (e.g., software, software modules) embodying any one or more of the methodologies or functions described herein. The software 222 may also reside, completely or at least partially, within main memory 204 and/or within processing device 202 during execution thereof by computer 200—main memory 204 and processing device 202 also constituting computer-accessible storage media. The software 222 may further be transmitted or received over a network 220 via network interface device 208.

While the computer-readable storage medium 230 is shown in an exemplary embodiment to be a single medium, the terms "computer-readable storage medium" and "machine-accessible storage medium" should be understood to include a single medium or multiple media (e.g., a centralized or distributed database, and/or associated caches and servers) that store the one or more sets of instructions. The term "computer-readable storage medium" should also be understood to include any medium that is capable of storing, encoding or carrying a set of instructions for execution by the computer and that cause the computer to perform any one or more of the methodologies of the present invention. The term "computer-readable storage medium" should accordingly be understood to include, but not be limited to, solid-state memories, optical and magnetic media, etc.

Exemplary System Platform

According to various embodiments, the processes and logic flows described in this specification may be performed by a system (e.g., System 100) that includes, but is not limited to, one or more programmable processors (e.g., processor 202) executing one or more computer program modules to perform functions by operating on input data and generating output, thereby tying the process to a particular machine (e.g., a machine programmed to perform the processes described herein). This includes processors located in one or more of client computers (e.g., client computers 140, 150, 160, 170, 180, 190 of FIG. 1). These devices connected to network 110 may access and execute one or more Internet browser-based program modules that are "served up" through the network 110 by one or more servers (e.g., server 120 of FIG. 1), and the data associated with the program may be stored on a one or more storage devices, which may reside within a server or computing device (e.g., Main Memory 204, Static Memory 206), be attached as a peripheral storage device to the one or more servers or computing devices, or attached to the network (e.g., Storage 130).

The System 100 facilitates the acquisition, storage, maintenance, use, and retention of campaign data associated with a plurality of privacy campaigns within an organization. In doing so, various aspects of the System 100 initiates and creates a plurality of individual data privacy campaign records that are associated with a variety of privacy-related attributes and assessment related meta-data for each campaign. These data elements may include: the subjects of the sensitive information, the respective person or entity responsible for each campaign (e.g., the campaign's "owner"), the location where the personal data will be stored, the entity or entities that will access the data, the parameters according to which the personal data will be used and retained, the Risk Level associated with a particular campaign (as well as assessments from which the Risk Level is calculated), an audit schedule, and other attributes and meta-data. The System 100 may also be adapted to facilitate the setup and auditing of each privacy campaign. These modules may include, for example, a Main Privacy Compliance Module, a Risk Assessment Module, a Privacy Audit Module, a Data Flow Diagram Module, and a Communications Module (examples of which are described below). It is to be understood that these are examples of modules of various embodiments, but the functionalities performed by each module as described may be performed by more (or less) modules. Further, the functionalities described as being performed by one module may be performed by one or more other modules.

A. Example Elements Related to Privacy Campaigns

Figure 3:
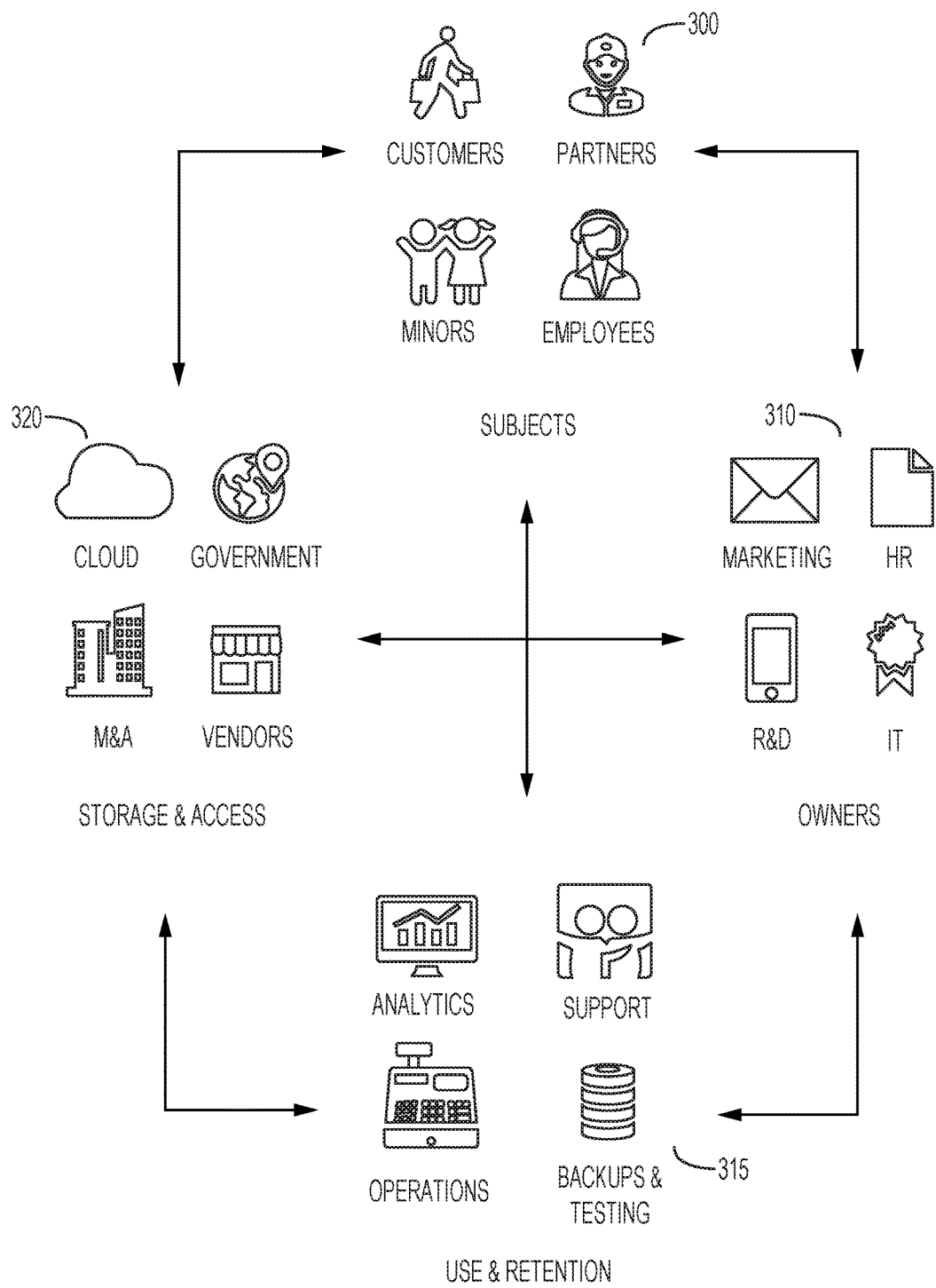
FIG. 3 is a diagram illustrating an example of the elements (e.g., subjects, owner, etc.) that may be involved in privacy compliance.

FIG. 3 provides a high-level visual overview of example "subjects" for particular data privacy campaigns, exemplary campaign "owners," various elements related to the storage and access of personal data, and elements related to the use and retention of the personal data. Each of these elements may, in various embodiments, be accounted for by the System 100 as it facilitates the implementation of an organization's privacy compliance policy.

As may be understood from FIG. 3, sensitive information may be collected by an organization from one or more subjects 300. Subjects may include customers whose information has been obtained by the organization. For example, if the organization is selling goods to a customer, the organization may have been provided with a customer's credit card or banking information (e.g., account number, bank routing number), social security number, or other sensitive information.

An organization may also possess personal data originating from one or more of its business partners. Examples of business partners are vendors that may be data controllers or data processors (which have different legal obligations under EU data protection laws). Vendors may supply a component or raw material to the organization, or an outside contractor responsible for the marketing or legal work of the organization. The personal data acquired from the partner may be that of the partners, or even that of other entities collected by the partners. For example, a marketing agency may collect personal data on behalf of the organization, and transfer that information to the organization. Moreover, the organization may share personal data with one of its partners. For example, the organization may provide a marketing agency with the personal data of its customers so that it may conduct further research.

Other subjects 300 include the organization's own employees. Organizations with employees often collect personal data from their employees, including address and social security information, usually for payroll purposes, or even prior to employment, for conducting credit checks. The subjects 300 may also include minors. It is noted that various corporate privacy policies or privacy laws may require that organizations take additional steps to protect the sensitive privacy of minors.

Still referring to FIG. 3, within an organization, a particular individual (or groups of individuals) may be designated to be an "owner" of a particular campaign to obtain and manage personal data. These owners 310 may have any suitable role within the organization. In various embodiments, an owner of a particular campaign will have primary responsibility for the campaign, and will serve as a resident expert regarding the personal data obtained through the campaign, and the way that the data is obtained, stored, and accessed. As shown in FIG. 3, an owner may be a member of any suitable department, including the organization's marketing, HR, R&D, or IT department. As will be described below, in exemplary embodiments, the owner can always be changed, and owners can sub-assign other owners (and other collaborators) to individual sections of campaign data input and operations.

Referring still to FIG. 3, the system may be configured to account for the use and retention 315 of personal data obtained in each particular campaign. The use and retention of personal data may include how the data is analyzed and used within the organization's operations, whether the data is backed up, and which parties within the organization are supporting the campaign.

The system may also be configured to help manage the storage and access 320 of personal data. As shown in FIG. 3, a variety of different parties may access the data, and the data may be stored in any of a variety of different locations, including on-site, or in "the cloud", i.e., on remote servers that are accessed via the Internet or other suitable network.

B. Main Compliance Module

Figure 4:
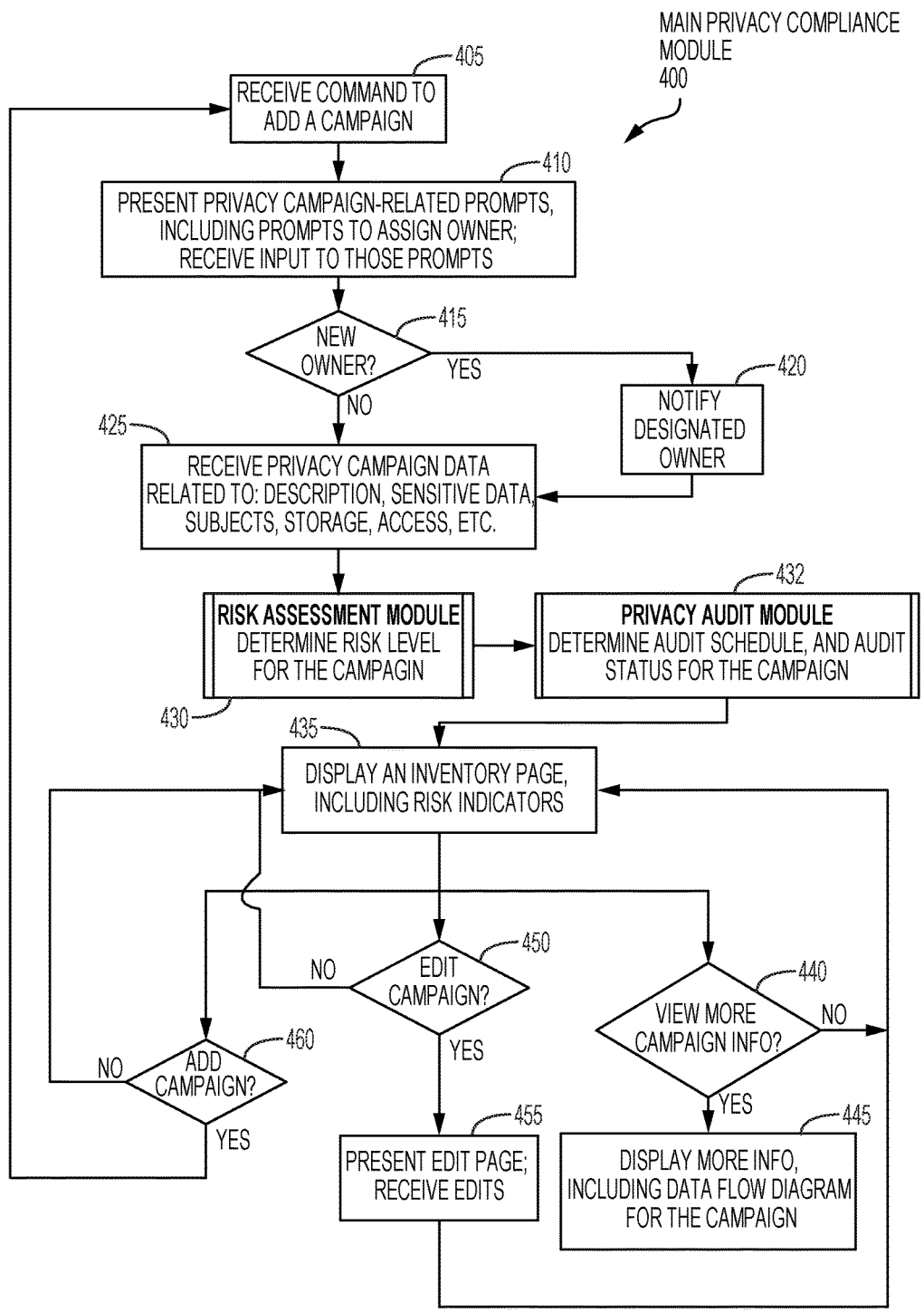
FIG. 4 is a flow chart showing an example of a process performed by the Main Privacy Compliance Module.

FIG. 4 illustrates an exemplary process for operationalizing privacy compliance. Main Privacy Compliance Module 400, which may be executed by one or more computing devices of System 100, may perform this process. In exemplary embodiments, a server (e.g., server 140) in conjunction with a client computing device having a browser, execute the Main Privacy Compliance Module (e.g., computing devices 140, 150, 160, 170, 180, 190) through a network (network 110). In various exemplary embodiments, the Main Privacy Compliance Module 400 may call upon other modules to perform certain functions. In exemplary embodiments, the software may also be organized as a single module to perform various computer executable routines.

I. Adding a Campaign

The process 400 may begin at step 405, wherein the Main Privacy Compliance Module 400 of the System 100 receives a command to add a privacy campaign. In exemplary embodiments, the user selects an on-screen button (e.g., the Add Data Flow button 1555 of FIG. 15) that the Main Privacy Compliance Module 400 displays on a landing page, which may be displayed in a graphical user interface (GUI), such as a window, dialog box, or the like. The landing page may be, for example, the inventory page 1500 below. The inventory page 1500 may display a list of one or more privacy campaigns that have already been input into the System 100. As mentioned above, a privacy campaign may represent, for example, a business operation that the organization is engaged in, or some business record, that may require the use of personal data, which may include the personal data of a customer or some other entity. Examples of campaigns might include, for example, Internet Usage History, Customer Payment Information, Call History Log, Cellular Roaming Records, etc. For the campaign "Internet Usage History," a marketing department may need customers' on-line browsing patterns to run analytics. This might entail retrieving and storing customers' IP addresses, MAC address, URL history, subscriber ID, and other information that may be considered personal data (and even sensitive personal data). As will be described herein, the System 100, through the use of one or more modules, including the Main Privacy Campaign Module 400, creates a record for each campaign. Data elements of campaign data may be associated with each campaign record that represents attributes such as: the type of personal data associated with the campaign; the subjects having access to the personal data;

the person or persons within the company that take ownership (e.g., business owner) for ensuring privacy compliance for the personal data associated with each campaign; the location of the personal data; the entities having access to the data; the various computer systems and software applications that use the personal data; and the Risk Level (see below) associated with the campaign.

II. Entry of Privacy Campaign Related Information, Including Owner

At Step 410, in Response to the Receipt of the User's Command to Add a Privacy campaign record, the Main Privacy Compliance Module 400 initiates a routine to create an electronic record for a privacy campaign, and a routine for the entry data inputs of information related to the privacy campaign. The Main Privacy Compliance Module 400 may generate one or more graphical user interfaces (e.g., windows, dialog pages, etc.), which may be presented one GUI at a time. Each GUI may show prompts, editable entry fields, check boxes, radial selectors, etc., where a user may enter or select privacy campaign data. In exemplary embodiments, the Main Privacy Compliance Module 400 displays on the graphical user interface a prompt to create an electronic record for the privacy campaign. A user may choose to add a campaign, in which case the Main Privacy Compliance Module 400 receives a command to create the electronic record for the privacy campaign, and in response to the command, creates a record for the campaign and digitally stores the record for the campaign. The record for the campaign may be stored in, for example, storage 130, or a storage device associated with the Main Privacy Compliance Module (e.g., a hard drive residing on Server 110, or a peripheral hard drive attached to Server 110).

The user may be a person who works in the Chief Privacy Officer's organization (e.g., a privacy office rep, or privacy officer). The privacy officer may be the user that creates the campaign record, and enters initial portions of campaign data (e.g., "high level" data related to the campaign), for example, a name for the privacy campaign, a description of the campaign, and a business group responsible for administering the privacy operations related to that campaign (for example, though the GUI shown in FIG. 6). The Main Privacy Compliance Module 400 may also prompt the user to enter a person or entity responsible for each campaign (e.g., the campaign's "owner"). The owner may be tasked with the responsibility for ensuring or attempting to ensure that the privacy policies or privacy laws associated with personal data related to a particular privacy campaign are being complied with. In exemplary embodiments, the default owner of the campaign may be the person who initiated the creation of the privacy campaign. That owner may be a person who works in the Chief Privacy Officer's organization (e.g., a privacy office rep, or privacy officer). The initial owner of the campaign may designate someone else to be the owner of the campaign. The designee may be, for example, a representative of some business unit within the organization (a business rep). Additionally, more than one owner may be assigned. For example, the user may assign a primary business rep, and may also assign a privacy office rep as owners of the campaign.

In many instances, some or most of the required information related to the privacy campaign record might not be within the knowledge of the default owner (i.e., the privacy office rep). The Main Data Compliance Module 400 can be operable to allow the creator of the campaign record (e.g., a privacy officer rep) to designate one or more other collaborators to provide at least one of the data inputs for the campaign data. Different collaborators, which may include the one or more owners, may be assigned to different questions, or to specific questions within the context of the privacy campaign. Additionally, different collaborators may be designated to respond to pats of questions. Thus, portions of campaign data may be assigned to different individuals.

Still referring to FIG. 4, if at step 415 the Main Privacy Compliance Module 400 has received an input from a user to designate a new owner for the privacy campaign that was created, then at step 420, the Main Privacy Compliance Module 400 may notify that individual via a suitable notification that the privacy campaign has been assigned to him or her. Prior to notification, the Main Privacy Compliance Module 400 may display a field that allows the creator of the campaign to add a personalized message to the newly assigned owner of the campaign to be included with that notification. In exemplary embodiments, the notification may be in the form of an email message. The email may include the personalized message from the assignor, a standard message that the campaign has been assigned to him/her, the deadline for completing the campaign entry, and instructions to log in to the system to complete the privacy campaign entry (along with a hyperlink that takes the user to a GUI providing access to the Main Privacy Compliance Module 400. Also included may be an option to reply to the email if an assigned owner has any questions, or a button that when clicked on, opens up a chat window (i.e., instant messenger window) to allow the newly assigned owner and the assignor a GUI in which they are able to communicate in real-time. An example of such a notification appears in FIG. 16 below. In addition to owners, collaborators that are assigned to input portions of campaign data may also be notified through similar processes. In exemplary embodiments, The Main Privacy Compliance Module 400 may, for example through a Communications Module, be operable to send collaborators emails regarding their assignment of one or more portions of inputs to campaign data. Or through the Communications Module, selecting the commentators button brings up one or more collaborators that are on-line (with the off-line users still able to see the messages when they are back on-line. Alerts indicate that one or more emails or instant messages await a collaborator.

At step 425, regardless of whether the owner is the user (i.e., the creator of the campaign), "someone else" assigned by the user, or other collaborators that may be designated with the task of providing one or more items of campaign data, the Main Privacy Campaign Module 400 may be operable to electronically receive campaign data inputs from one or more users related to the personal data related to a privacy campaign through a series of displayed computer-generated graphical user interfaces displaying a plurality of prompts for the data inputs. In exemplary embodiments, through a step-by-step process, the Main Privacy Campaign Module may receive from one or more users' data inputs that include campaign data like: (1) a description of the campaign; (2) one or more types of personal data to be collected and stored as part of the campaign; (3) individuals from which the personal data is to be collected; (4) the storage location of the personal data, and (5) information regarding who will have access to the personal data. These inputs may be obtained, for example, through the graphical user interfaces shown in FIGS. 8 through 13, wherein the Main Compliance Module 400 presents on sequentially appearing GUIs the prompts for the entry of each of the enumerated campaign data above. The Main Compliance Module 400 may process the campaign data by electronically associating the campaign data with the record for the campaign and digitally storing the campaign data with the record for the campaign. The campaign data may be digitally stored as data elements in a database residing in a memory location in the server 120, a peripheral storage device attached to the server, or one or more storage devices connected to the network (e.g., storage 130). If campaign data inputs have been assigned to one or more collaborators, but those collaborators have not input the data yet, the Main Compliance Module 400 may, for example through the Communications Module, sent an electronic message (such as an email) alerting the collaborators and owners that they have not yet supplied their designated portion of campaign data.

III. Privacy Campaign Information Display

At step 430, Main Privacy Compliance Module 400 may, in exemplary embodiments, call upon a Risk Assessment Module 430 that may determine and assign a Risk Level for the privacy campaign, based wholly or in part on the information that the owner(s) have input. The Risk Assessment Module 430 will be discussed in more detail below.

At step 432, Main Privacy Compliance Module 400 may in exemplary embodiments, call upon a Privacy Audit Module 432 that may determine an audit schedule for each privacy campaign, based, for example, wholly or in part on the campaign data that the owner(s) have input, the Risk Level assigned to a campaign, and/or any other suitable factors. The Privacy Audit Module 432 may also be operable to display the status of an audit for each privacy campaign. The Privacy Audit Module 432 will be discussed in more detail below.

At step 435, the Main Privacy Compliance Module 400 may generate and display a GUI showing an inventory page (e.g., inventory page 1500) that includes information associated with each campaign. That information may include information input by a user (e.g., one or more owners), or information calculated by the Main Privacy Compliance Module 400 or other modules. Such information may include for example, the name of the campaign, the status of the campaign, the source of the campaign, the storage location of the personal data related to the campaign, etc. The inventory page 1500 may also display an indicator representing the Risk Level (as mentioned, determined for each campaign by the Risk Assessment Module 430), and audit information related to the campaign that was determined by the Privacy Audit Module (see below). The inventory page 1500 may be the landing page displayed to users that access the system. Based on the login information received from the user, the Main Privacy Compliance Module may determine which campaigns and campaign data the user is authorized to view, and display only the information that the user is authorized to view. Also from the inventory page 1500, a user may add a campaign (discussed above in step 405), view more information for a campaign, or edit information related to a campaign (see, e.g., FIGS. 15, 16, 17).

If other commands from the inventory page are received (e.g., add a campaign, view more information, edit information related to the campaign), then step 440, 445, and/or 450 may be executed.

At step 440, if a command to view more information has been received or detected, then at step 445, the Main Privacy Compliance Module 400 may present more information about the campaign, for example, on a suitable campaign information page 1500. At this step, the Main Privacy Compliance Module 400 may invoke a Data Flow Diagram Module (described in more detail below). The Data Flow Diagram Module may generate a flow diagram that shows, for example, visual indicators indicating whether data is confidential and/or encrypted (see, e.g., FIG. 1600 below).

At step 450, if the system has received a request to edit a campaign, then, at step 455, the system may display a dialog page that allows a user to edit information regarding the campaign (e.g., edit campaign dialog 1700).

At step 460, if the system has received a request to add a campaign, the process may proceed back to step 405.

C. Risk Assessment Module

Figure 5:
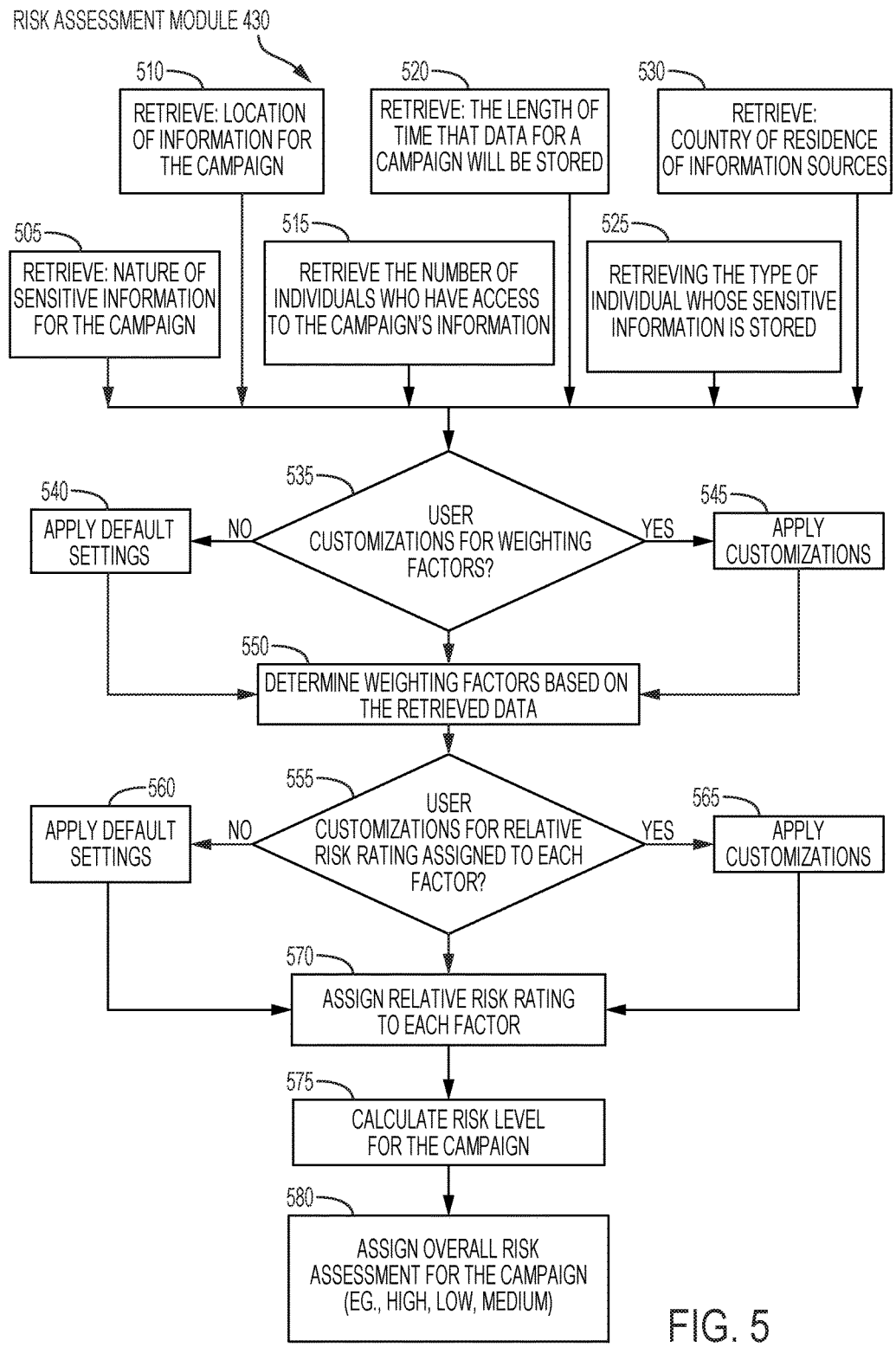
FIG. 5 is a flow chart showing an example of a process performed by the Risk Assessment Module.

FIG. 5 illustrates an exemplary process for determining a Risk Level and Overall Risk Assessment for a particular privacy campaign performed by Risk Assessment Module 430.

I. Determining Risk Level

In exemplary embodiments, the Risk Assessment Module 430 may be operable to calculate a Risk Level for a campaign based on the campaign data related to the personal data associated with the campaign. The Risk Assessment Module may associate the Risk Level with the record for the campaign and digitally store the Risk Level with the record for the campaign.

The Risk Assessment Module 430 may calculate this Risk Level based on any of various factors associated with the campaign. The Risk Assessment Module 430 may determine a plurality of weighting factors based upon, for example: (1) the nature of the sensitive information collected as part of the campaign (e.g., campaigns in which medical information, financial information or non-public personal identifying information is collected may be indicated to be of higher risk than those in which only public information is collected, and thus may be assigned a higher numerical weighting factor); (2) the location in which the information is stored (e.g., campaigns in which data is stored in the cloud may be deemed higher risk than campaigns in which the information is stored locally); (3) the number of individuals who have access to the information (e.g., campaigns that permit relatively large numbers of individuals to access the personal data may be deemed more risky than those that allow only small numbers of individuals to access the data); (4) the length of time that the data will be stored within the system (e.g., campaigns that plan to store and use the personal data over a long period of time may be deemed more risky than those that may only hold and use the personal data for a short period of time); (5) the individuals whose sensitive information will be stored (e.g., campaigns that involve storing and using information of minors may be deemed of greater risk than campaigns that involve storing and using the information of adults); (6) the country of residence of the individuals whose sensitive information will be stored (e.g., campaigns that involve collecting data from individuals that live in countries that have relatively strict privacy laws may be deemed more risky than those that involve collecting data from individuals that live in countries that have relative lax privacy laws). It should be understood that any other suitable factors may be used to assess the Risk Level of a particular campaign, including any new inputs that may need to be added to the risk calculation.

In particular embodiments, one or more of the individual factors may be weighted (e.g., numerically weighted) according to the deemed relative importance of the factor relative to other factors (i.e., Relative Risk Rating).

These weightings may be customized from organization to organization, and/or according to different applicable laws. In particular embodiments, the nature of the sensitive information will be weighted higher than the storage location of the data, or the length of time that the data will be stored.

In various embodiments, the system uses a numerical formula to calculate the Risk Level of a particular campaign.

This formula may be, for example: Risk Level for campaign=(Weighting Factor of Factor 1)*(Relative Risk Rating of Factor 1)+(Weighting Factor of Factor 2)*(Relative Risk Rating of Factor 2)+ . . . (Weighting Factor of Factor N)*(Relative Risk Rating of Factor N). As a simple example, the Risk Level for a campaign that only collects publicly available information for adults and that stores the information locally for a short period of several weeks might be determined as Risk Level=(Weighting Factor of Nature of Sensitive Information)*(Relative Risk Rating of Particular Sensitive Information to be Collected)+(Weighting Factor of Individuals from which Information is to be Collected)*(Relative Risk Rating of Individuals from which Information is to be Collected)+(Weighting Factor of Duration of Data Retention)*(Relative Risk Rating of Duration of Data Retention)+(Weighting Factor of Individuals from which Data is to be Collected)*(Relative Risk Rating of Individuals from which Data is to be Collected). In this example, the Weighting Factors may range, for example from 1-5, and the various Relative Risk Ratings of a factor may range from 1-10. However, the system may use any other suitable ranges.

In particular embodiments, the Risk Assessment Module 430 may have default settings for assigning Overall Risk Assessments to respective campaigns based on the numerical Risk Level value determined for the campaign, for example, as described above. The organization may also modify these settings in the Risk Assessment Module 430 by assigning its own Overall Risk Assessments based on the numerical Risk Level. For example, the Risk Assessment Module 430 may, based on default or user assigned settings, designate: (1) campaigns with a Risk Level of 1-7 as "low risk" campaigns, (2) campaigns with a Risk Level of 8-15 as "medium risk" campaigns; (3) campaigns with a Risk Level of over 16 as "high risk" campaigns. As show below, in an example inventory page 1500, the Overall Risk Assessment for each campaign can be indicated by up/down arrow indicators, and further, the arrows may have different shading (or color, or portions shaded) based upon this Overall Risk Assessment. The selected colors may be conducive for viewing by those who suffer from color blindness.

Thus, the Risk Assessment Module 430 may be configured to automatically calculate the numerical Risk Level for each campaign within the system, and then use the numerical Risk Level to assign an appropriate Overall Risk Assessment to the respective campaign. For example, a campaign with a Risk Level of 5 may be labeled with an Overall Risk Assessment as "Low Risk". The system may associate both the Risk Level and the Overall Risk Assessment with the campaign and digitally store them as part of the campaign record.

II. Exemplary Process for Assessing Risk

Accordingly, as shown in FIG. 5, in exemplary embodiments, the Risk Assessment Module 430 electronically retrieves from a database (e.g., storage device 130) the campaign data associated with the record for the privacy campaign. It may retrieve this information serially, or in parallel. At step 505, the Risk Assessment Module 430 retrieves information regarding (1) the nature of the sensitive information collected as part of the campaign. At step 510, the Risk Assessment Module 430 retrieves information regarding the (2) the location in which the information related to the privacy campaign is stored. At step 515, the Risk Assessment Module 430 retrieves information regarding (3) the number of individuals who have access to the information. At step 520, the Risk Assessment Module retrieves information regarding (4) the length of time that the data associated with a campaign will be stored within the System 100. At step 525, the Risk Assessment Module retrieves information regarding (5) the individuals whose sensitive information will be stored. At step 530, the Risk Assessment Module retrieves information regarding (6) the country of residence of the individuals whose sensitive information will be stored.

At step 535, the Risk Assessment Module takes into account any user customizations to the weighting factors related to each of the retrieved factors from steps 505, 510, 515, 520, 525, and 530. At steps 540 and 545, the Risk Assessment Module applies either default settings to the weighting factors (which may be based on privacy laws), or customizations to the weighting factors. At step 550, the Risk Assessment Module determines a plurality of weighting factors for the campaign. For example, for the factor related to the nature of the sensitive information collected as part of the campaign, a weighting factor of 1-5 may be assigned based on whether non-public personal identifying information is collected.

At step 555, the Risk Assessment Module takes into account any user customizations to the Relative Risk assigned to each factor, and at step 560 and 565, will either apply default values (which can be based on privacy laws) or the customized values for the Relative Risk. At step 570, the Risk Assessment Module assigns a relative risk rating for each of the plurality of weighting factors. For example, the relative risk rating for the location of the information of the campaign may be assigned a numerical number (e.g., from 1-10) that is lower than the numerical number assigned to the Relative Risk Rating for the length of time that the sensitive information for that campaign is retained.

At step 575, the Risk Assessment Module 430 calculates the relative risk assigned to the campaign based upon the plurality of Weighting Factors and the Relative Risk Rating for each of the plurality of factors. As an example, the Risk Assessment Module 430 may make this calculation using the formula of Risk Level=(Weighting Factor of Factor 1)*(Relative Risk Rating of Factor 1)+(Weighting Factor of Factor 2)*(Relative Risk Rating of Factor 2)+ . . . (Weighting Factor of Factor N)*(Relative Risk Rating of Factor N).

At step 580, based upon the numerical value derived from step 575, the Risk Assessment Module 430 may determine an Overall Risk Assessment for the campaign. The Overall Risk Assessment determination may be made for the privacy campaign may be assigned based on the following criteria, which may be either a default or customized setting: (1) campaigns with a Risk Level of 1-7 as "low risk" campaigns, (2) campaigns with a Risk Level of 8-15 as "medium risk" campaigns; (3) campaigns with a Risk Level of over 16 as "high risk" campaigns. The Overall Risk Assessment is then associated and stored with the campaign record.

D. Privacy Audit Module

The System 100 may determine an audit schedule for each campaign, and indicate, in a particular graphical user interface (e.g., inventory page 1500), whether a privacy audit is coming due (or is past due) for each particular campaign and, if so, when the audit is/was due. The System 100 may also be operable to provide an audit status for each campaign, and alert personnel of upcoming or past due privacy audits. To further the retention of evidence of compliance, the System 100 may also receive and store evidence of compliance. A Privacy Audit Module 432, may facilitate these functions.

I. Determining a Privacy Audit Schedule and Monitoring Compliance

In exemplary embodiments, the Privacy Audit Module 432 is adapted to automatically schedule audits and manage compliance with the audit schedule. In particular embodiments, the system may allow a user to manually specify an audit schedule for each respective campaign. The Privacy Audit Module 432 may also automatically determine, and save to memory, an appropriate audit schedule for each respective campaign, which in some circumstances, may be editable by the user.

The Privacy Audit Module 432 may automatically determine the audit schedule based on the determined Risk Level of the campaign. For example, all campaigns with a Risk Level less than 10 may have a first audit schedule and all campaigns with a Risk Level of 10 or more may have a second audit schedule. The Privacy Audit Module may also be operable determine the audit schedule based on the Overall Risk Assessment for the campaign (e.g., "low risk" campaigns may have a first predetermined audit schedule, "medium risk" campaigns may have a second predetermined audit schedule, "high risk" campaigns may have a third predetermined audit schedule, etc.).

In particular embodiments, the Privacy Audit Module 432 may automatically facilitate and monitor compliance with the determined audit schedules for each respective campaign. For example, the system may automatically generate one or more reminder emails to the respective owners of campaigns as the due date approaches. The system may also be adapted to allow owners of campaigns, or other users, to submit evidence of completion of an audit (e.g., by for example, submitting screen shots that demonstrate that the specified parameters of each campaign are being followed). In particular embodiments, the system is configured for, in response to receiving sufficient electronic information documenting completion of an audit, resetting the audit schedule (e.g., scheduling the next audit for the campaign according to a determined audit schedule, as determined above).

II. Exemplary Privacy Audit Process

Figure 6:
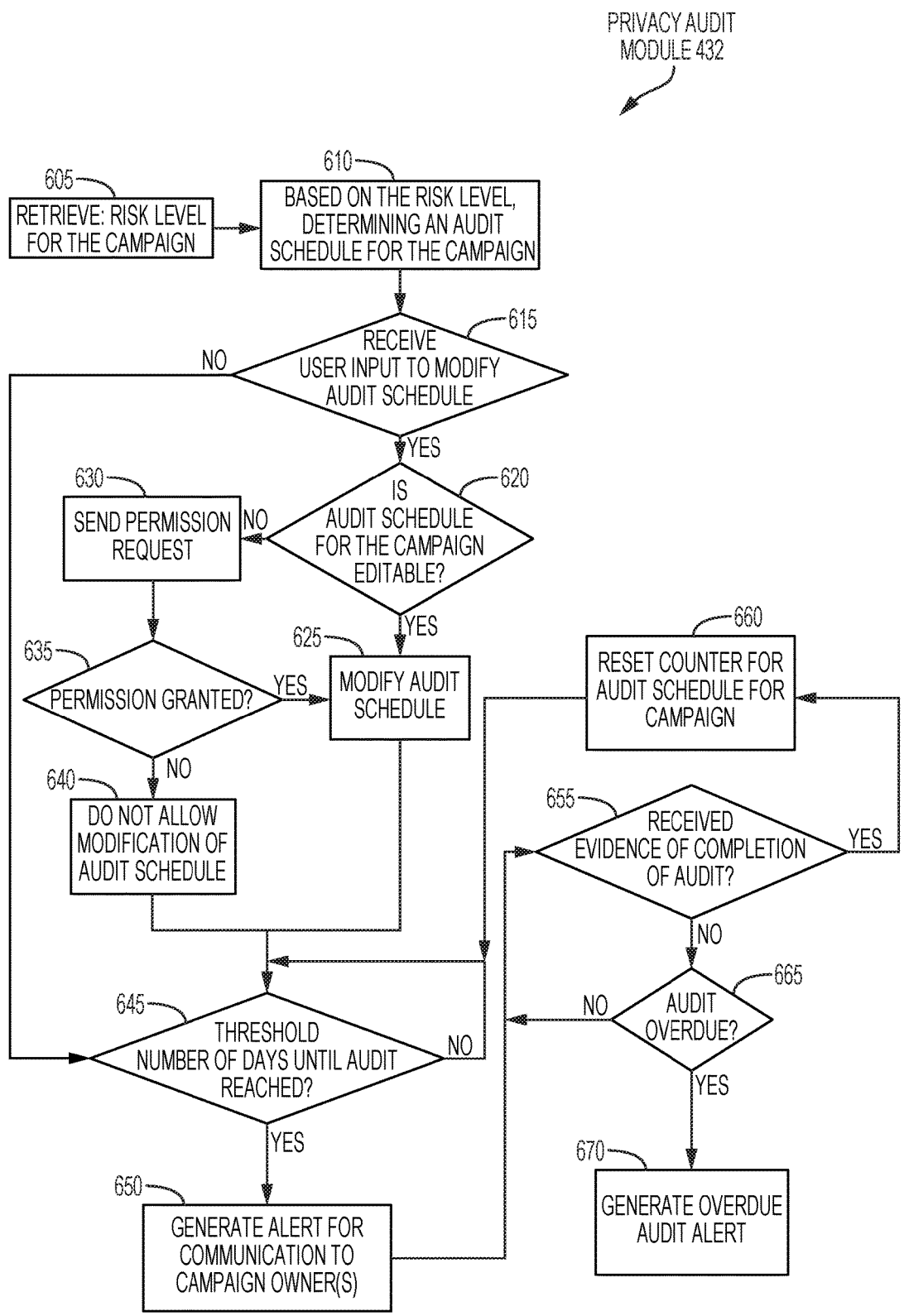
FIG. 6 is a flow chart showing an example of a process performed by the Privacy Audit Module.

FIG. 6 illustrates an exemplary process performed by a Privacy Audit Module 432 for assigning a privacy audit schedule and facilitating and managing compliance for a particular privacy campaign. At step 605, the Privacy Audit Module 432 retrieves the Risk Level associated with the privacy campaign. In exemplary embodiments, the Risk Level may be a numerical number, as determined above by the Risk Assessment Module 430. If the organization chooses, the Privacy Audit Module 432 may use the Overall Risk Assessment to determine which audit schedule for the campaign to assign.

At step 610, based on the Risk Level of the campaign (or the Overall Risk Assessment), or based on any other suitable factor, the Privacy Audit Module 432 can assign an audit schedule for the campaign. The audit schedule may be, for example, a timeframe (i.e., a certain amount of time, such as number of days) until the next privacy audit on the campaign to be performed by the one or more owners of the campaign. The audit schedule may be a default schedule. For example, the Privacy Audit Module can automatically apply an audit schedule of 120 days for any campaign having Risk Level of 10 and above. These default schedules may be modifiable. For example, the default audit schedule for campaigns having a Risk Level of 10 and above can be changed from 120 days to 150 days, such that any campaign having a Risk Level of 10 and above is assigned the customized default audit schedule (i.e., 150 days). Depending on privacy laws, default policies, authority overrides, or the permission level of the user attempting to modify this default, the default might not be modifiable.

At step 615, after the audit schedule for a particular campaign has already been assigned, the Privacy Audit Module 432 determines if a user input to modify the audit schedule has been received. If a user input to modify the audit schedule has been received, then at step 620, the Privacy Audit Module 432 determines whether the audit schedule for the campaign is editable (i.e., can be modified). Depending on privacy laws, default policies, authority overrides, or the permission level of the user attempting to modify the audit schedule, the campaign's audit schedule might not be modifiable.

At step 625, if the audit schedule is modifiable, then the Privacy Audit Module will allow the edit and modify the audit schedule for the campaign. If at step 620 the Privacy Audit Module determines that the audit schedule is not modifiable, in some exemplary embodiments, the user may still request permission to modify the audit schedule. For example, the Privacy Audit Module 432 can at step 630 provide an indication that the audit schedule is not editable, but also provide an indication to the user that the user may contact through the system one or more persons having the authority to grant or deny permission to modify the audit schedule for the campaign (i.e., administrators) to gain permission to edit the field. The Privacy Audit Module 432 may display an on-screen button that, when selected by the user, sends a notification (e.g., an email) to an administrator. The user can thus make a request to the modify the audit schedule for the campaign in this manner.

At step 635, the Privacy Audit Module may determine whether permission has been granted by an administrator to allow a modification to the audit schedule. It may make this determination based on whether it has received input from an administrator to allow modification of the audit schedule for the campaign. If the administrator has granted permission, the Privacy Audit Module 432 at step 635 may allow the edit of the audit schedule. If at step 640, a denial of permission is received from the administrator, or if a certain amount of time has passed (which may be customized or based on a default setting), the Privacy Audit Module 432 retains the audit schedule for the campaign by not allowing any modifications to the schedule, and the process may proceed to step 645. The Privacy Audit Module may also send a reminder to the administrator that a request to modify the audit schedule for a campaign is pending.

At step 645, the Privacy Audit Module 432 determines whether a threshold amount of time (e.g., number of days) until the audit has been reached. This threshold may be a default value, or a customized value. If the threshold amount of time until an audit has been reached, the Privacy Audit Module 432 may at step 650 generate an electronic alert. The alert can be a message displayed to the collaborator the next time the collaborator logs into the system, or the alert can be an electronic message sent to one or more collaborators, including the campaign owners. The alert can be, for example, an email, an instant message, a text message, or one or more of these communication modalities. For example, the message may state, "This is a notification that a privacy audit for Campaign Internet Browsing History is scheduled to occur in 90 days." More than one threshold may be assigned, so that the owner of the campaign receives more than one alert as the scheduled privacy audit deadline approaches. If the threshold number of days has not been reached, the Privacy Audit Module 432 will continue to evaluate whether the threshold has been reached (i.e., back to step 645).

In exemplary embodiments, after notifying the owner of the campaign of an impending privacy audit, the Privacy Audit Module may determine at step 655 whether it has received any indication or confirmation that the privacy audit has been completed. In example embodiments, the Privacy Audit Module allows for evidence of completion to be submitted, and if sufficient, the Privacy Audit Module 432 at step 660 resets the counter for the audit schedule for the campaign. For example, a privacy audit may be confirmed upon completion of required electronic forms in which one or more collaborators verify that their respective portions of the audit process have been completed. Additionally, users can submit photos, screen shots, or other documentation that show that the organization is complying with that user's assigned portion of the privacy campaign. For example, a database administrator may take a screen shot showing that all personal data from the privacy campaign is being stored in the proper database and submit that to the system to document compliance with the terms of the campaign.

If at step 655, no indication of completion of the audit has been received, the Privacy Audit Module 432 can determine at step 665 whether an audit for a campaign is overdue (i.e., expired). If it is not overdue, the Privacy Audit Module 432 will continue to wait for evidence of completion (e.g., step 655). If the audit is overdue, the Privacy Audit Module 432 at step 670 generates an electronic alert (e.g., an email, instant message, or text message) to the campaign owner(s) or other administrators indicating that the privacy audit is overdue, so that the organization can take responsive or remedial measures.

In exemplary embodiments, the Privacy Audit Module 432 may also receive an indication that a privacy audit has begun (not shown), so that the status of the audit when displayed on inventory page 1500 shows the status of the audit as pending. While the audit process is pending, the Privacy Audit Module 432 may be operable to generate reminders to be sent to the campaign owner(s), for example, to remind the owner of the deadline for completing the audit.

E. Data Flow Diagram Module

The system 110 may be operable to generate a data flow diagram based on the campaign data entered and stored, for example in the manner described above.

I. Display of Security Indicators and Other Information

In various embodiments, a Data Flow Diagram Module is operable to generate a flow diagram for display containing visual representations (e.g., shapes) representative of one or more parts of campaign data associated with a privacy campaign, and the flow of that information from a source (e.g., customer), to a destination (e.g., an internet usage database), to which entities and computer systems have access (e.g., customer support, billing systems). Data Flow Diagram Module may also generate one or more security indicators for display. The indicators may include, for example, an "eye" icon to indicate that the data is confidential, a "lock" icon to indicate that the data, and/or a particular flow of data, is encrypted, or an "unlocked lock" icon to indicate that the data, and/or a particular flow of data, is not encrypted. In the example shown in FIG. 16, the dotted arrow lines generally depict respective flows of data and the locked or unlocked lock symbols indicate whether those data flows are encrypted or unencrypted. The color of dotted lines representing data flows may also be colored differently based on whether the data flow is encrypted or non-encrypted, with colors conducive for viewing by those who suffer from color blindness.

II. Exemplary Process Performed by Data Flow Diagram Module

Figure 7:
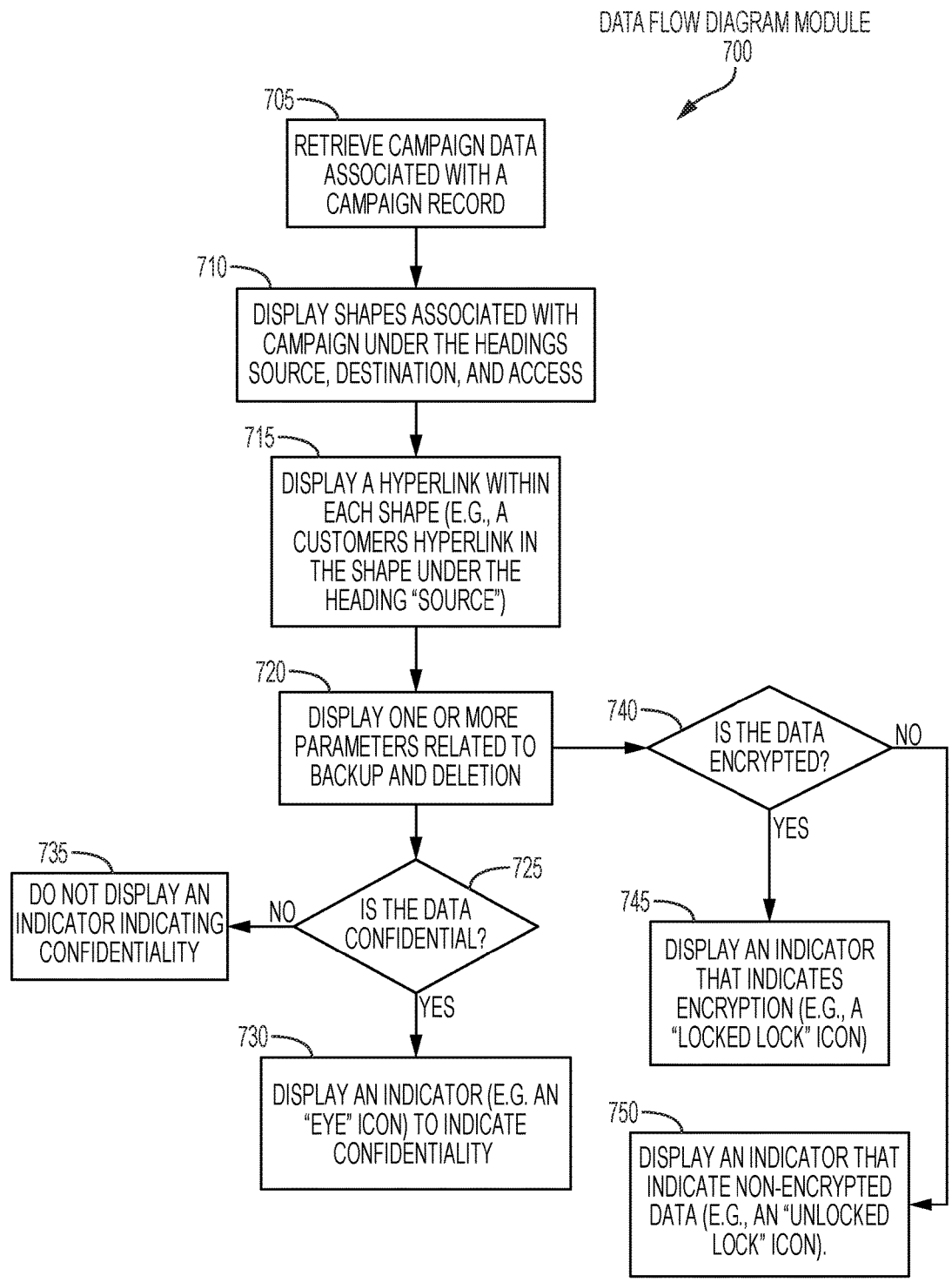
FIG. 7 is a flow chart showing an example of a process performed by the Data Flow Diagram Module.

FIG. 7 shows an example process performed by the Data Flow Diagram Module 700. At step 705, the Data Flow Diagram retrieves campaign data related to a privacy campaign record. The campaign data may indicate, for example, that the sensitive information related to the privacy campaign contains confidential information, such as the social security numbers of a customer.

Figure 16:
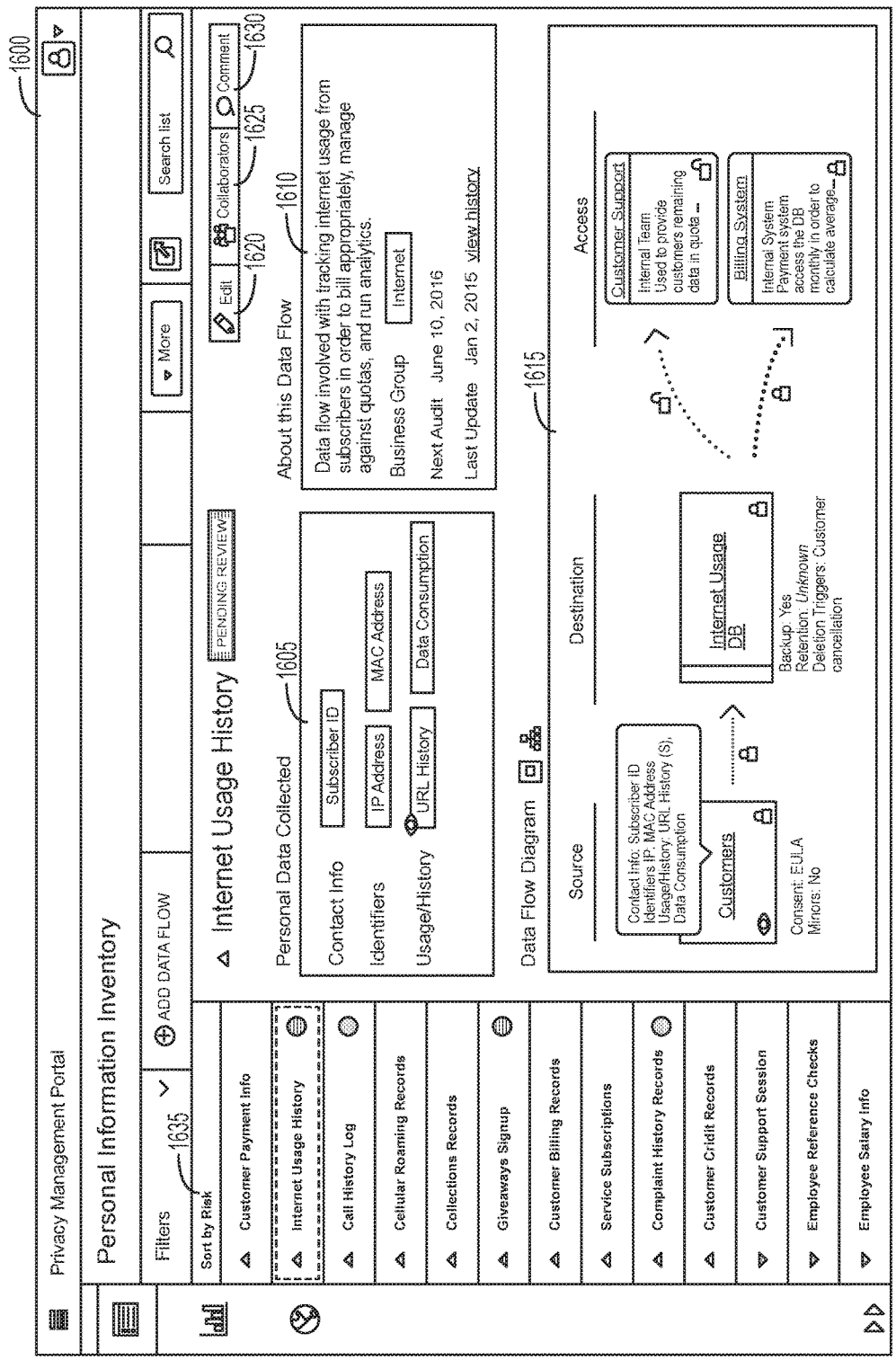
FIG. 16 is an example of a GUI showing campaign data, including a data flow diagram.

At step 710, the Data Flow Diagram Module 700 is operable to display on-screen objects (e.g., shapes) representative of the Source, Destination, and Access, which indicate that information below the heading relates to the source of the personal data, the storage destination of the personal data, and access related to the personal data. In addition to campaign data regarding Source, Destination, and Access, the Data Flow Diagram Module 700 may also account for user defined attributes related to personal data, which may also be displayed as on-screen objects. The shape may be, for example, a rectangular box (see, e.g., FIG. 16). At step 715, the Data Flow Diagram Module 700 may display a hyperlink label within the on-screen object (e.g., as shown in FIG. 16, the word "Customer" may be a hyperlink displayed within the rectangular box) indicative of the source of the personal data, the storage destination of the personal data, and access related to the personal data, under each of the respective headings. When a user hovers over the hyperlinked word, the Data Flow Diagram is operable to display additional campaign data relating to the campaign data associated with the hyperlinked word. The additional information may also be displayed in a pop up, or a new page. For example, FIG. 16 shows that if a user hovers over the words "Customer," the Data Flow Diagram Module 700 displays what customer information is associated with the campaign (e.g., the Subscriber ID, the IP and Mac Addresses associated with the Customer, and the customer's browsing and usage history). The Data Flow Diagram Module 700 may also generate for display information relating to whether the source of the data includes minors, and whether consent was given by the source to use the sensitive information, as well as the manner of the consent (for example, through an End User License Agreement (EULA)).

At step 720, the Data Flow Diagram Module 700 may display one or more parameters related to backup and retention of personal data related to the campaign, including in association with the storage destination of the personal data. As an example, Data Flow Diagram 1615 of FIG. 16 displays that the information in the Internet Usage database is backed up, and the retention related to that data is Unknown.

At 725, the Data Flow Diagram Module 700 determines, based on the campaign data associated with the campaign, whether the personal data related to each of the hyperlink labels is confidential. At Step 730, if the personal data related to each hyperlink label is confidential, the Data Flow Diagram Module 700 generates visual indicator indicating confidentiality of that data (e.g., an "eye" icon, as show in Data Flow Diagram 1615). If there is no confidential information for that box, then at step 735, no indicators are displayed. While this is an example of the generation of indicators for this particular hyperlink, in exemplary embodiments, any user defined campaign data may visual indicators that may be generated for it.

Figure 9:
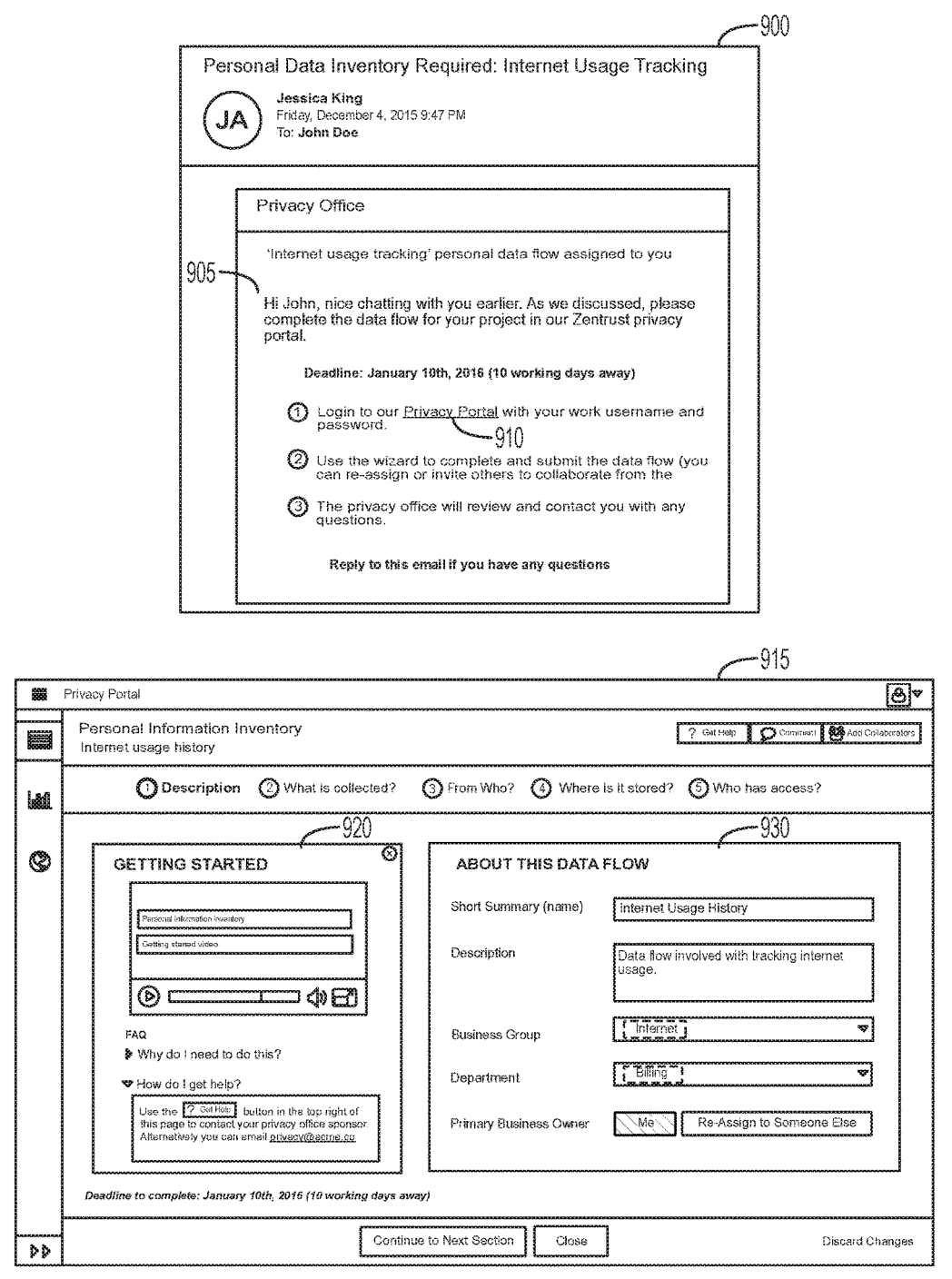

At step 740, the Data Flow Diagram Module 700 determined whether any of the data associated with the source, stored in a storage destination, being used by an entity or application, or flowing to one or more entities or systems (i.e., data flow) associated with the campaign is designated as encrypted. If the data is encrypted, then at step 745 the Data Flow Diagram Module 700 may generate an indicator that the personal data is encrypted (e.g., a "lock" icon). If the data is non-encrypted, then at step 750, the Data Flow Diagram Module 700 displays an indicator to indicate that the data or particular flow of data is not encrypted. (e.g., an "unlocked lock" icon). An example of a data flow diagram is depicted in FIG. 9. Additionally, the data flow diagram lines may be colored differently to indicate whether the data flow is encrypted or unencrypted, wherein the colors can still be distinguished by a color-blind person.

F. Communications Module

In exemplary embodiments, a Communications Module of the System 100 may facilitate the communications between various owners and personnel related to a privacy campaign. The Communications Module may retain contact information (e.g., emails or instant messaging contact information) input by campaign owners and other collaborators. The Communications Module can be operable to take a generated notification or alert (e.g., alert in step 670 generated by Privacy Audit Module 432) and instantiate an email containing the relevant information. As mentioned above, the Main Privacy Compliance Module 400 may, for example through a communications module, be operable to send collaborators emails regarding their assignment of one or more portions of inputs to campaign data. Or through the communications module, selecting the commentators button brings up one or more collaborators that are on-line In exemplary embodiments, the Communications Module can also, in response to a user request (e.g., depressing the "comment" button show in FIG. 9, FIG. 10, FIG. 11, FIG. 12, FIG. 13, FIG. 16), instantiate an instant messaging session and overlay the instant messaging session over one or more portions of a GUI, including a GUI in which a user is presented with prompts to enter or select information. An example of this instant messaging overlay feature orchestrated by the Communications Module is shown in FIG. 17. While a real-time message session may be generated, off-line users may still able to see the messages when they are back on-line.

The Communications Module may facilitate the generation of alerts that indicate that one or more emails or instant messages await a collaborator.

If campaign data inputs have been assigned to one or more collaborators, but those collaborators have not input the data yet, the Communications Module, may facilitate the sending of an electronic message (such as an email) alerting the collaborators and owners that they have not yet supplied their designated portion of campaign data.

Exemplary User Experience

In the exemplary embodiments of the system for operationalizing privacy compliance, adding a campaign (i.e., data flow) comprises gathering information that includes several phases: (1) a description of the campaign; (2) the personal data to be collected as part of the campaign; (3) who the personal data relates to; (4) where the personal data be stored; and (5) who will have access to the indicated personal data.

Figure 8:
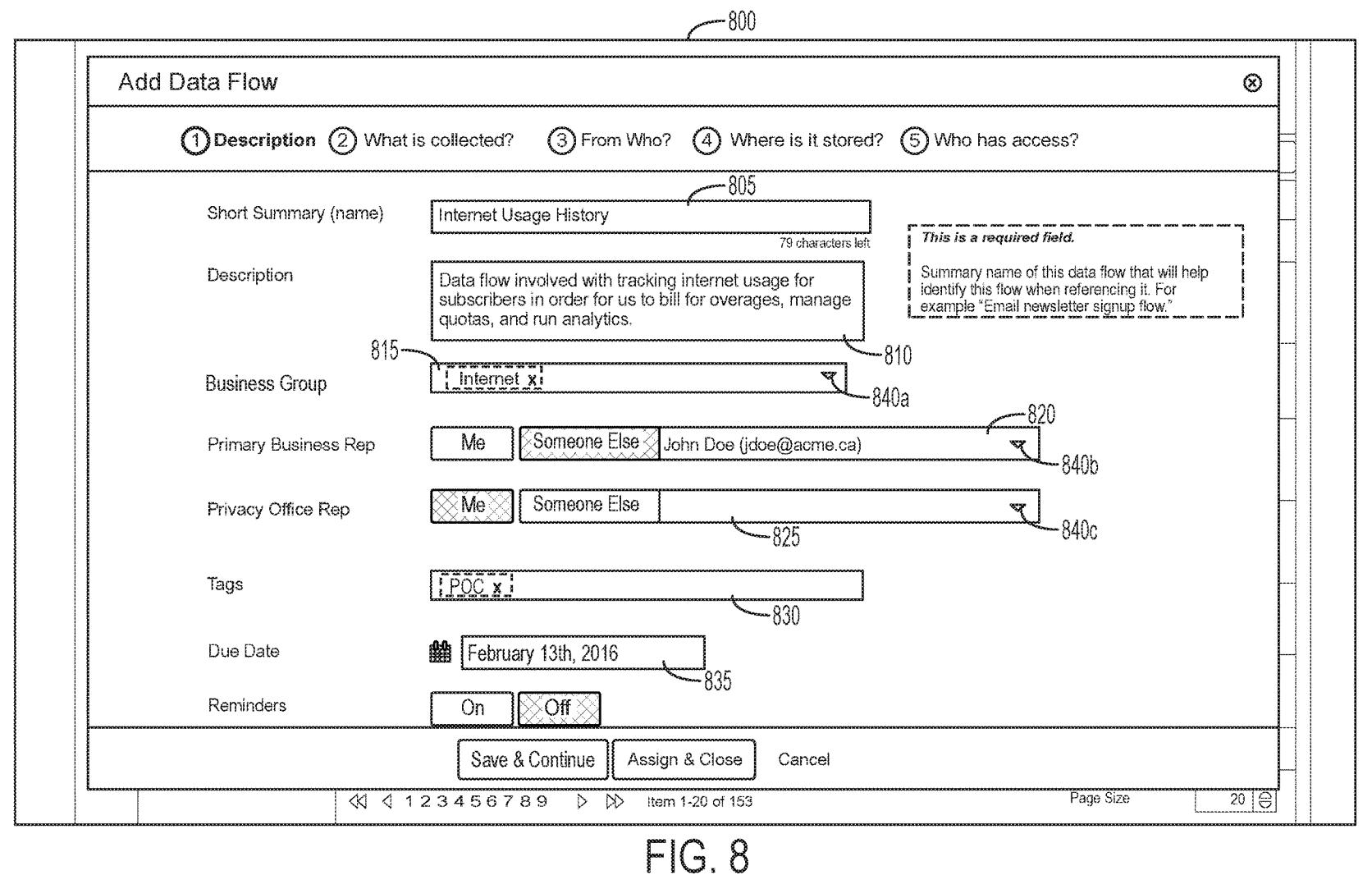

A. FIG. 8: Campaign Record Creation and Collaborator Assignment

FIG. 8 illustrates an example of the first phase of information gathering to add a campaign. In FIG. 8, a description entry dialog 800 may have several fillable/editable fields and drop-down selectors. In this example, the user may fill out the name of the campaign in the Short Summary (name) field 805, and a description of the campaign in the Description field 810. The user may enter or select the name of the business group (or groups) that will be accessing personal data for the campaign in the Business Group field 815. The user may select the primary business representative responsible for the campaign (i.e., the campaign's owner), and designate him/herself, or designate someone else to be that owner by entering that selection through the Someone Else field 820. Similarly, the user may designate him/herself as the privacy office representative owner for the campaign, or select someone else from the second Someone Else field 825. At any point, a user assigned as the owner may also assign others the task of selecting or answering any question related to the campaign. The user may also enter one or more tag words associated with the campaign in the Tags field 830. After entry, the tag words may be used to search for campaigns, or used to filter for campaigns (for example, under Filters 845). The user may assign a due date for completing the campaign entry, and turn reminders for the campaign on or off. The user may save and continue, or assign and close.

In example embodiments, some of the fields may be filled in by a user, with suggest-as-you-type display of possible field entries (e.g., Business Group field 815), and/or may include the ability for the user to select items from a drop-down selector (e.g., drop-down selectors 840*a*, 840*b*, 840*c*). The system may also allow some fields to stay hidden or unmodifiable to certain designated viewers or categories of users. For example, the purpose behind a campaign may be hidden from anyone who is not the chief privacy officer of the company, or the retention schedule may be configured so that it cannot be modified by anyone outside of the organization's' legal department.

B. FIG. 9: Collaborator Assignment Notification and Description Entry

Moving to FIG. 9, in example embodiments, if another business representative (owner), or another privacy office representative has been assigned to the campaign (e.g., John Doe in FIG. 8), the system may send a notification (e.g., an electronic notification) to the assigned individual, letting them know that the campaign has been assigned to him/her. FIG. 9 shows an example notification 900 sent to John Doe that is in the form of an email message. The email informs him that the campaign "Internet Usage Tracking" has been assigned to him, and provides other relevant information, including the deadline for completing the campaign entry and instructions to log in to the system to complete the campaign (data flow) entry (which may be done, for example, using a suitable "wizard" program). The user that assigned John ownership of the campaign may also include additional comments 905 to be included with the notification 900. Also included may be an option to reply to the email if an assigned owner has any questions.

In this example, if John selects the hyperlink Privacy Portal 910, he is able to access the system, which displays a landing page 915. The landing page 915 displays a Getting Started section 920 to familiarize new owners with the system, and also displays an "About This Data Flow" section 930 showing overview information for the campaign.

Figure 10:
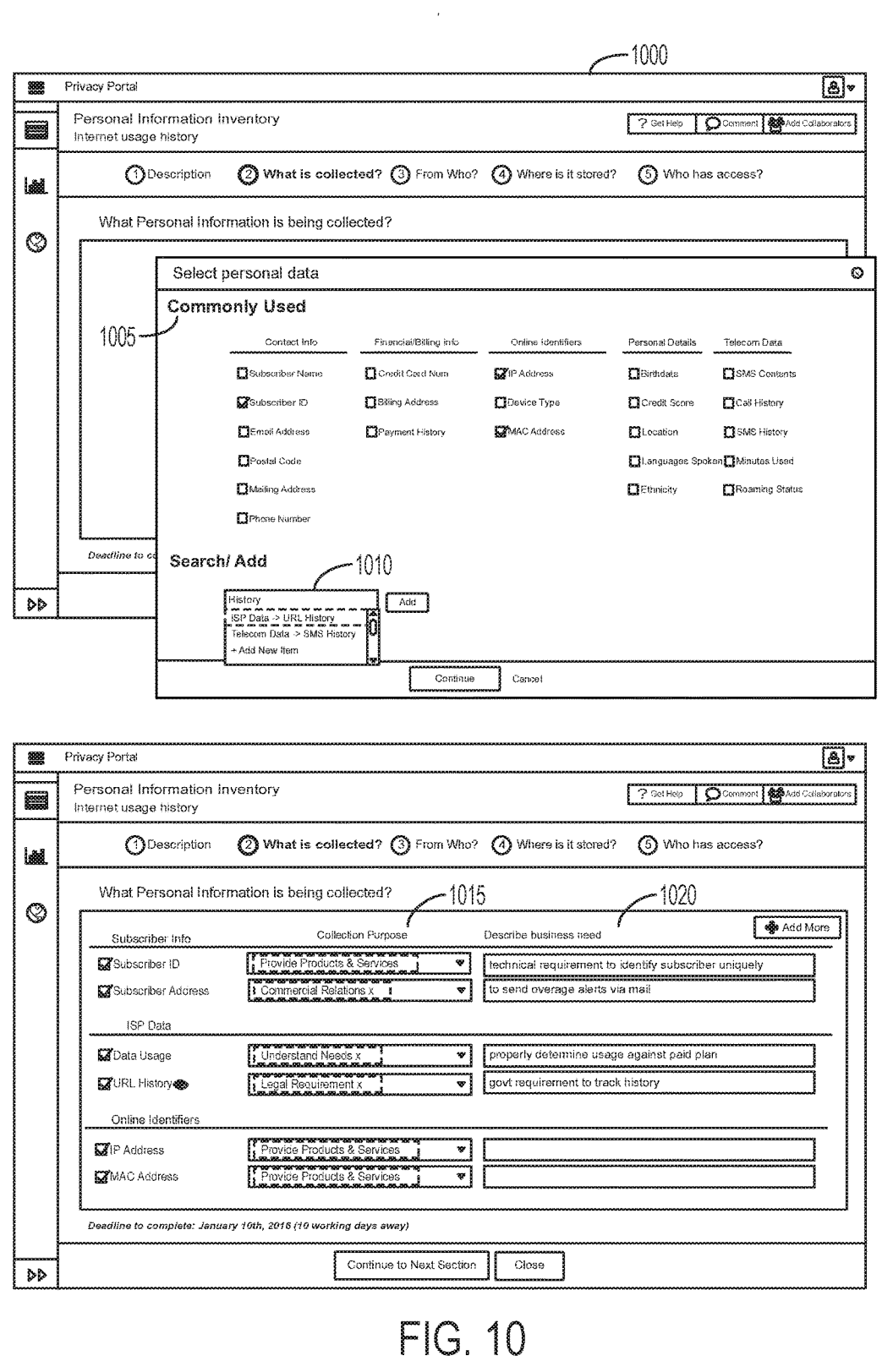

C. FIG. 10: What Personal Data is Collected

Moving to FIG. 10, after the first phase of campaign addition (i.e., description entry phase), the system may present the user (who may be a subsequently assigned business representative or privacy officer) with a dialog 1000 from which the user may enter in the type of personal data being collected.

In addition, questions are described generally as transitional questions, but the questions may also include one or more smart questions in which the system is configured to: (1) pose an initial question to a user and, (2) in response to the user's answer satisfying certain criteria, presenting the user with one or more follow-up questions. For example, in FIG. 10, if the user responds with a choice to add personal data, the user may be additionally presented follow-up prompts, for example, the select personal data window overlaying screen 800 that includes commonly used selections may include, for example, particular elements of an individual's contact information (e.g., name, address, email address), Financial/Billing Information (e.g., credit card number, billing address, bank account number), Online Identifiers (e.g., IP Address, device type, MAC Address), Personal Details (Birthdate, Credit Score, Location), or Telecommunication Data (e.g., Call History, SMS History, Roaming Status). The System 100 is also operable to pre-select or automatically populate choices—for example, with commonly-used selections 1005, some of the boxes may already be checked. The user may also use a search/add tool 1010 to search for other selections that are not commonly used and add another selection. Based on the selections made, the user may be presented with more options and fields. For example, if the user selected "Subscriber ID" as personal data associated with the campaign, the user may be prompted to add a collection purpose under the heading Collection Purpose 1015, and the user may be prompted to provide the business reason why a Subscriber ID is being collected under the "Describe Business Need" heading 1020.

Figure 11:
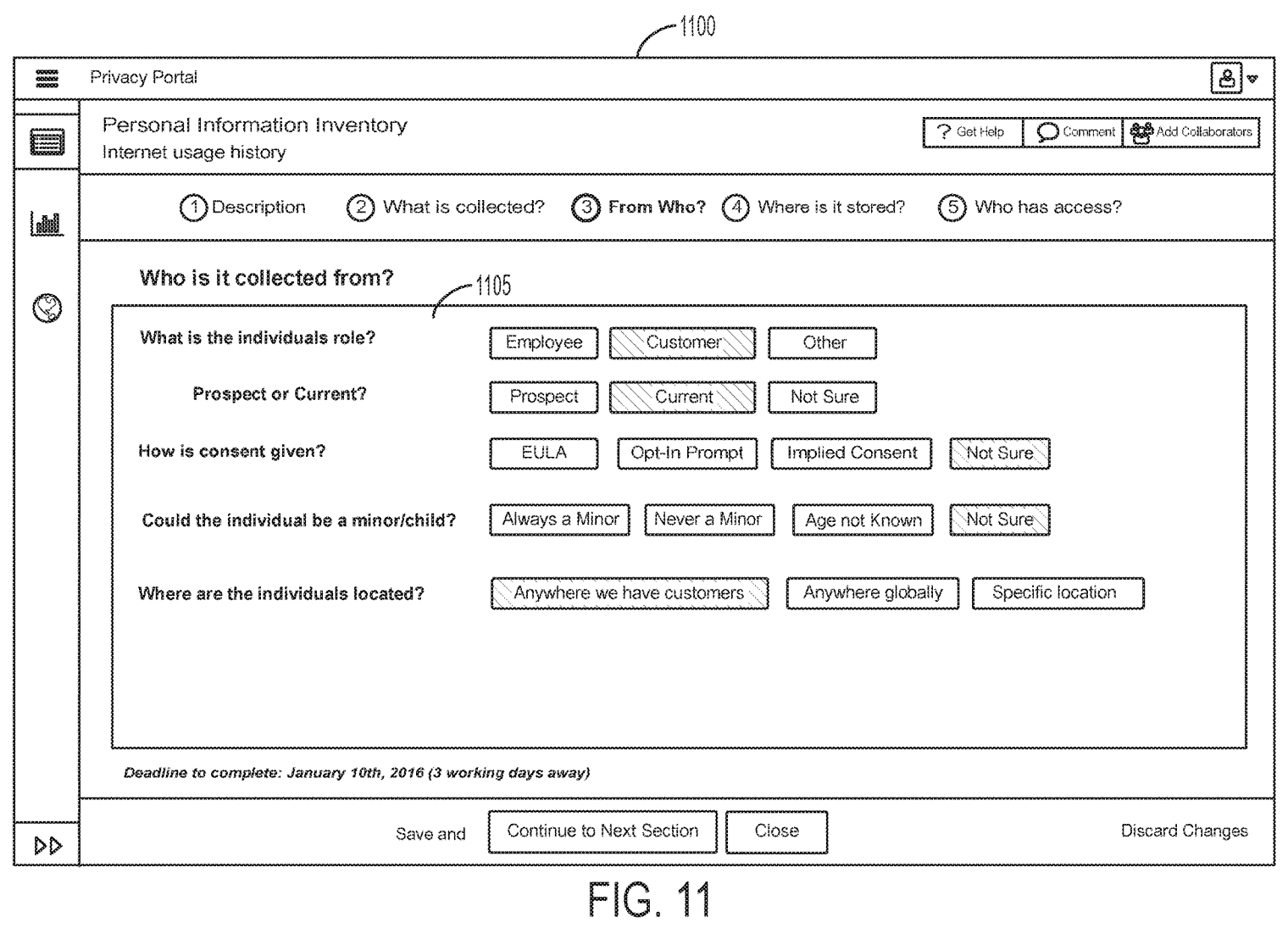

D. FIG. 11: Who Personal Data is Collected from

As displayed in the example of FIG. 11, the third phase of adding a campaign may relate to entering and selecting information regarding who the personal data is gathered from. As noted above, the personal data may be gathered from, for example, one or more Subjects 100. In the exemplary "Collected From" dialog 1100, a user may be presented with several selections in the "Who Is It Collected From" section 1105. These selections may include whether the personal data was to be collected from an employee, customer, or other entity. Any entities that are not stored in the system may be added. The selections may also include, for example, whether the data was collected from a current or prospective subject (e.g., a prospective employee may have filled out an employment application with his/her social security number on it). Additionally, the selections may include how consent was given, for example through an end user license agreement (EULA), on-line Opt-in prompt, Implied consent, or an indication that the user is not sure. Additional selections may include whether the personal data was collected from a minor, and where the subject is located.

Figure 12:
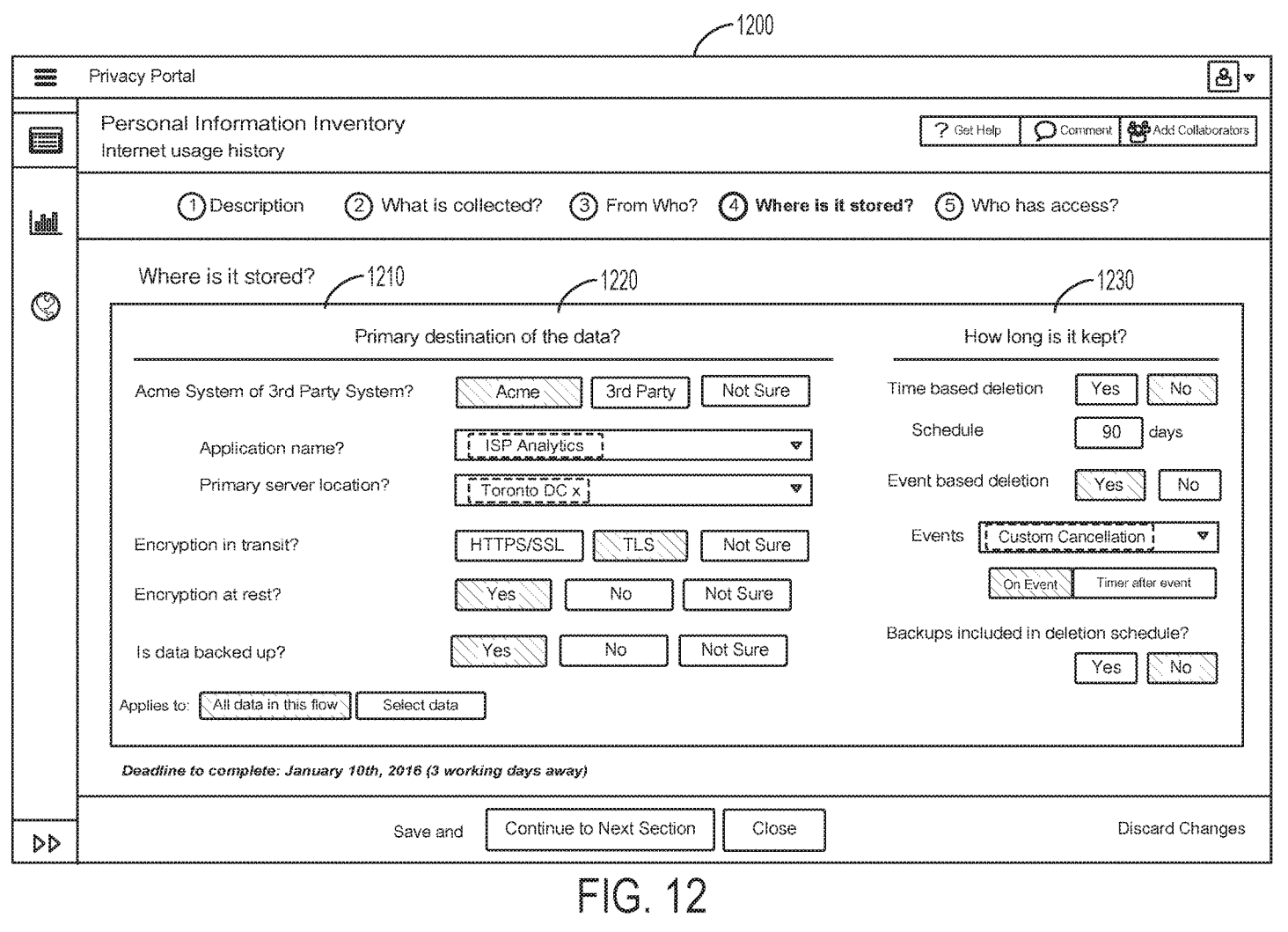

E. FIG. 12: Where is the Personal Data Stored

FIG. 12 shows an example "Storage Entry" dialog screen 1200, which is a graphical user interface that a user may use to indicate where particular sensitive information is to be stored within the system. From this section, a user may specify, in this case for the Internet Usage History campaign, the primary destination of the personal data 1220 and how long the personal data is to be kept 1230. The personal data may be housed by the organization (in this example, an entity called "Acme") or a third party. The user may specify an application associated with the personal data's storage (in this example, ISP Analytics), and may also specify the location of computing systems (e.g., servers) that will be storing the personal data (e.g., a Toronto data center). Other selections indicate whether the data will be encrypted and/or backed up.

The system also allows the user to select whether the destination settings are applicable to all the personal data of the campaign, or just select data (and if so, which data). In FIG. 12, the user may also select and input options related to the retention of the personal data collected for the campaign (e.g., How Long Is It Kept 1230). The retention options may indicate, for example, that the campaign's personal data should be deleted after a per-determined period of time has passed (e.g., on a particular date), or that the campaign's personal data should be deleted in accordance with the occurrence of one or more specified events (e.g., in response to the occurrence of a particular event, or after a specified period of time passes after the occurrence of a particular event), and the user may also select whether backups should be accounted for in any retention schedule. For example, the user may specify that any backups of the personal data should be deleted (or, alternatively, retained) when the primary copy of the personal data is deleted.

Figure 13:
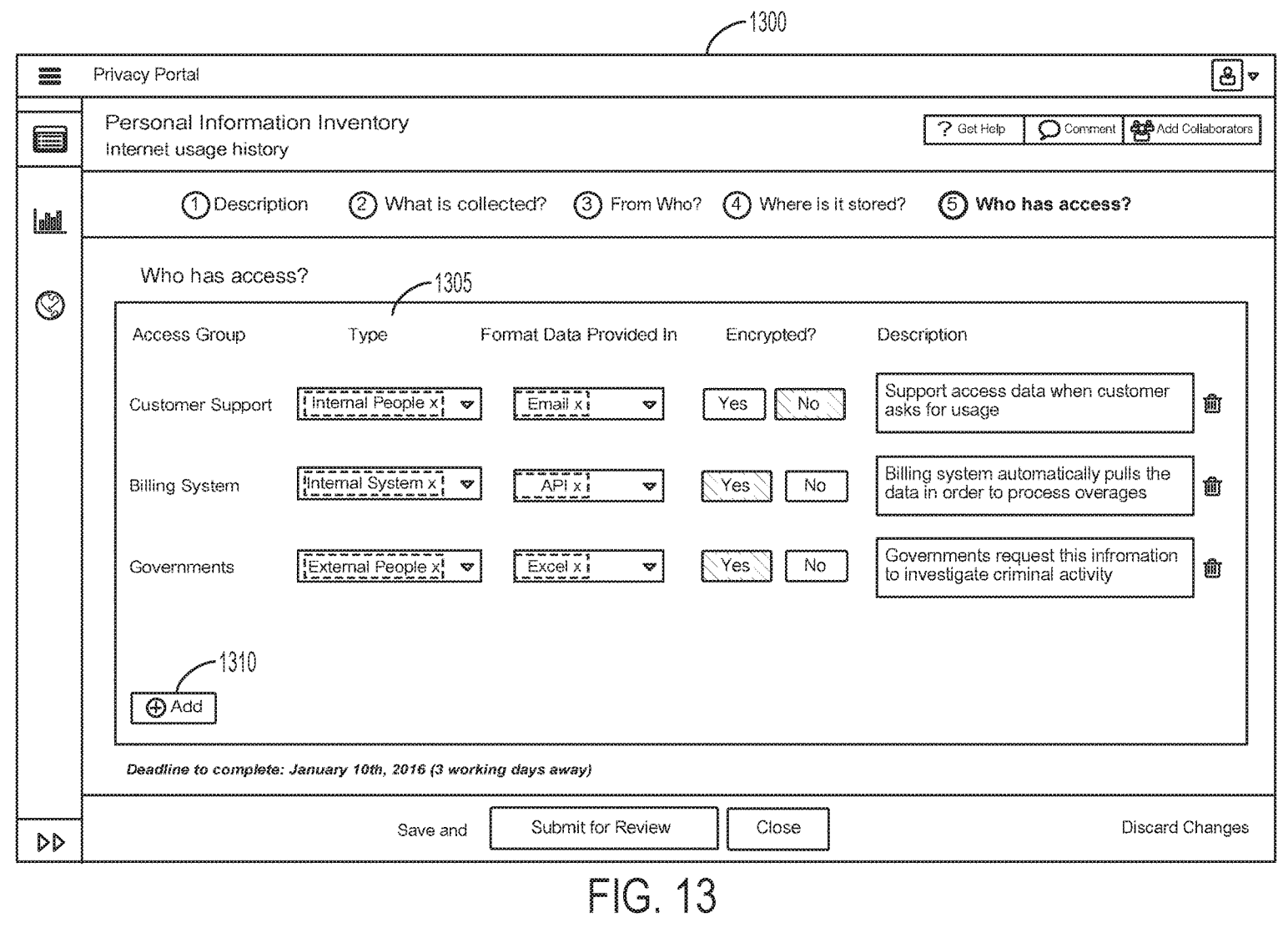

F. FIG. 13: Who and What Systems have Access to Personal Data

FIG. 13 describes an example Access entry dialog screen 1300. As part of the process of adding a campaign or data flow, the user may specify in the "Who Has Access" section 1305 of the dialog screen 1300. In the example shown, the Customer Support, Billing, and Government groups within the organization are able to access the Internet Usage History personal data collected by the organization. Within each of these access groups, the user may select the type of each group, the format in which the personal data was provided, and whether the personal data is encrypted. The access level of each group may also be entered. The user may add additional access groups via the Add Group button 1310.

G. Facilitating Entry of Campaign Data, Including Chat Shown in FIG. 14

As mentioned above, to facilitate the entry of data collected through the example GUIs shown in FIGS. 8 through 12, in exemplary embodiments, the system is adapted to allow the owner of a particular campaign (or other user) to assign certain sections of questions, or individual questions, related to the campaign to contributors other than the owner. This may eliminate the need for the owner to contact other users to determine information that they don't know and then enter the information into the system themselves. Rather, in various embodiments, the system facilitates the entry of the requested information directly into the system by the assigned users.

In exemplary embodiments, after the owner assigns a respective responsible party to each question or section of questions that need to be answered in order to fully populate the data flow, the system may automatically contact each user (e.g., via an appropriate electronic message) to inform the user that they have been assigned to complete the specified questions and/or sections of questions, and provide those users with instructions as to how to log into the system to enter the data. The system may also be adapted to periodically follow up with each user with reminders until the user completes the designated tasks. As discussed elsewhere herein, the system may also be adapted to facilitate real-time text or voice communications between multiple collaborators as they work together to complete the questions necessary to define the data flow. Together, these features may reduce the amount of time and effort needed to complete each data flow.

Figure 14:
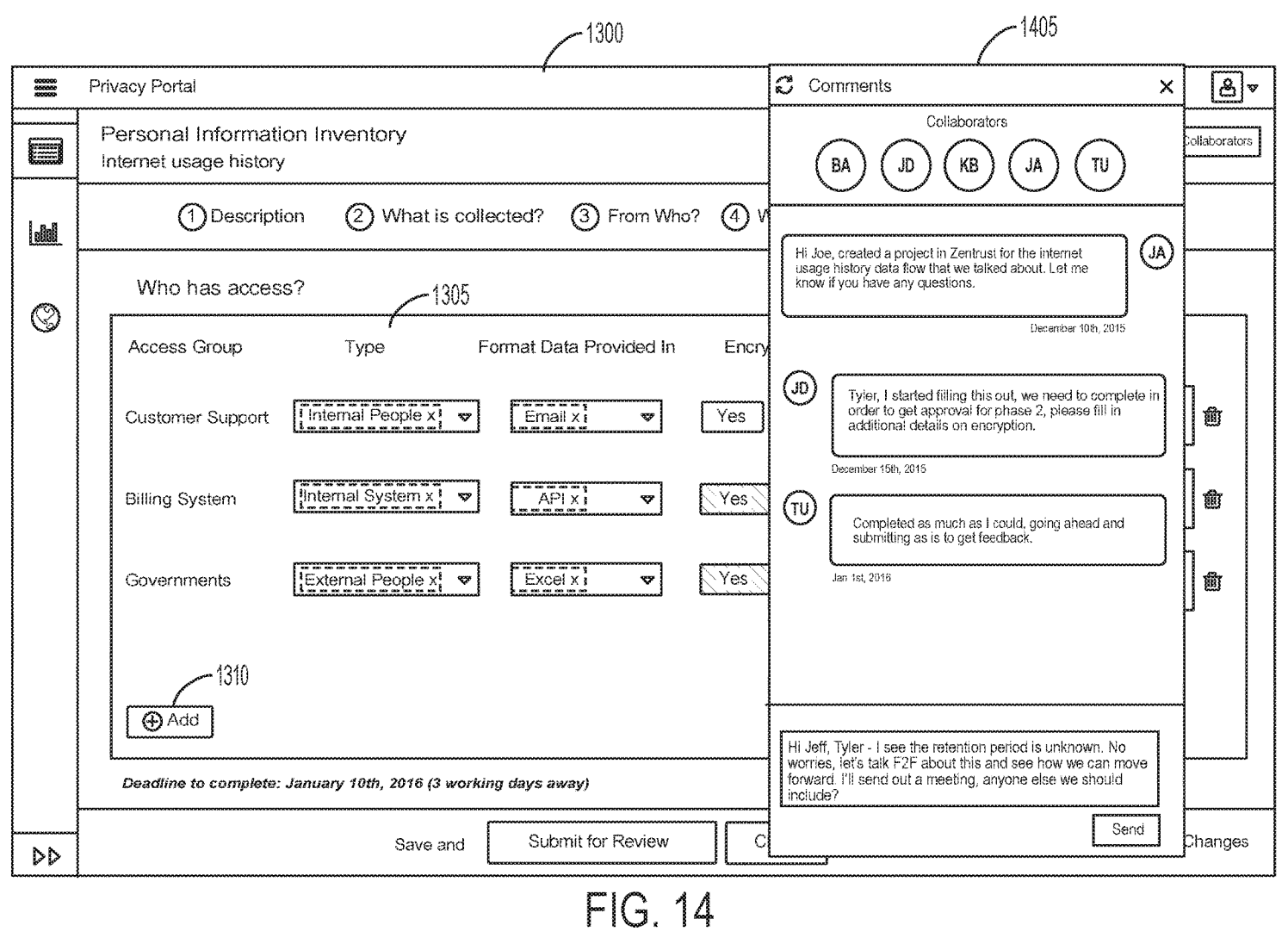

To further facilitate collaboration, as shown FIG. 14, in exemplary embodiments, the System 100 is operable to overlay an instant messaging session over a GUI in which a user is presented with prompts to enter or select information. In FIG. 14, a communications module is operable to create an instant messaging session window 1405 that overlays the Access entry dialog screen 1400. In exemplary embodiments, the Communications Module, in response to a user request (e.g., depressing the "comment" button show in FIG. 9, FIG. 10, FIG. 11, FIG. 12, FIG. 13, FIG. 16), instantiates an instant messaging session and overlays the instant messaging session over one or more portions of the GUI.

Figure 15:
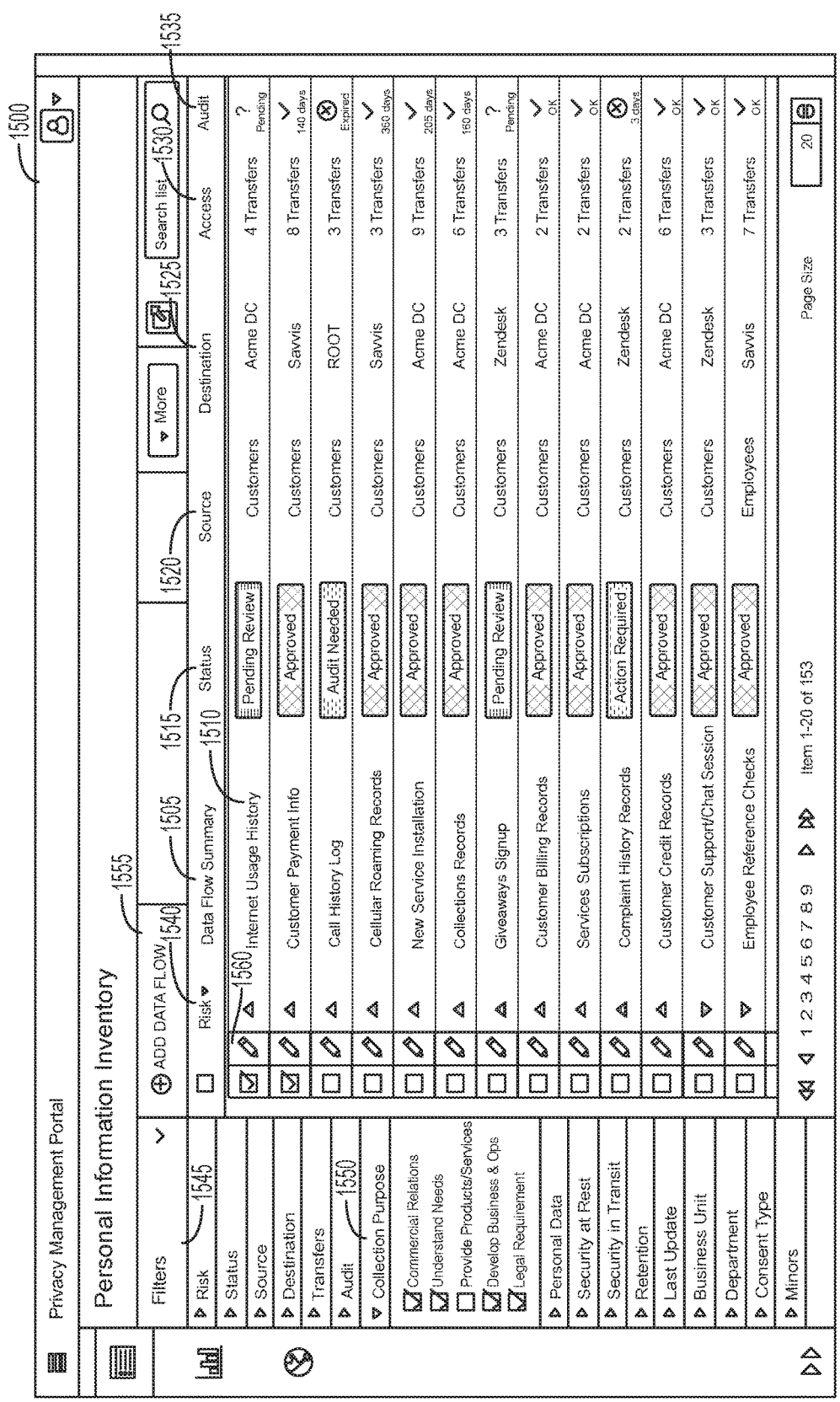
FIG. 15 is an example of a GUI showing an inventory page.

H: FIG. 15: Campaign Inventory Page

After new campaigns have been added, for example using the exemplary processes explained in regard to FIGS. 8-13, the users of the system may view their respective campaign or campaigns, depending on whether they have access to the campaign. The chief privacy officer, or another privacy office representative, for example, may be the only user that may view all campaigns. A listing of all of the campaigns within the system may be viewed on, for example, inventory page 1500 (see below). Further details regarding each campaign may be viewed via, for example, campaign information page 1600, which may be accessed by selecting a particular campaign on the inventory page 1500. And any information related to the campaign may be edited or added through, for example, the edit campaign dialog 1700 screen. Certain fields or information may not be editable, depending on the particular user's level of access. A user may also add a new campaign using a suitable user interface, such as the graphical user interface shown in FIG. 15 or FIG. 16.

In example embodiments, the System 100 (and more particularly, the Main Privacy Compliance Module 400) may use the history of past entries to suggest selections for users during campaign creation and entry of associated data. As an example, in FIG. 10, if most entries that contain the term "Internet" and have John Doe as the business rep assigned to the campaign have the items Subscriber ID, IP Address, and MAC Address selected, then the items that are commonly used may display as pre-selected items the Subscriber ID, IP address, and MAC Address each time a campaign is created having Internet in its description and John Doe as its business rep.

FIG. 15 describes an example embodiment of an inventory page 1500 that may be generated by the Main Privacy Compliance Module 400. The inventory page 1500 may be represented in a graphical user interface. Each of the graphical user interfaces (e.g., webpages, dialog boxes, etc.) presented in this application may be, in various embodiments, an HTML-based page capable of being displayed on a web browser (e.g., Firefox, Internet Explorer, Google Chrome, Opera, etc.), or any other computer-generated graphical user interface operable to display information, including information having interactive elements (e.g., an iOS, Mac OS, Android, Linux, or Microsoft Windows application). The webpage displaying the inventory page 1500 may include typical features such as a scroll-bar, menu items, as well as buttons for minimizing, maximizing, and closing the webpage. The inventory page 1500 may be accessible to the organization's chief privacy officer, or any other of the organization's personnel having the need, and/or permission, to view personal data.

Still referring to FIG. 15, inventory page 1500 may display one or more campaigns listed in the column heading Data Flow Summary 1505, as well as other information associated with each campaign, as described herein. Some of the exemplary listed campaigns include Internet Usage History 1510, Customer Payment Information, Call History Log, Cellular Roaming Records, etc. A campaign may represent, for example, a business operation that the organization is engaged in may require the use of personal data, which may include the personal data of a customer. In the campaign Internet Usage History 1510, for example, a marketing department may need customers' on-line browsing patterns to run analytics. Examples of more information that may be associated with the Internet Usage History 1510 campaign will be presented in FIG. 4 and FIG. 5. In example embodiments, clicking on (i.e., selecting) the column heading Data Flow Summary 1505 may result in the campaigns being sorted either alphabetically, or reverse alphabetically.

The inventory page 1500 may also display the status of each campaign, as indicated in column heading Status 1515. Exemplary statuses may include "Pending Review", which means the campaign has not been approved yet, "Approved," meaning the data flow associated with that campaign has been approved, "Audit Needed," which may indicate that a privacy audit of the personal data associated with the campaign is needed, and "Action Required," meaning that one or more individuals associated with the campaign must take some kind of action related to the campaign (e.g., completing missing information, responding to an outstanding message, etc.). In certain embodiments, clicking on (i.e., selecting) the column heading Status 1515 may result in the campaigns being sorted by status.

The inventory page 1500 of FIG. 15 may list the "source" from which the personal data associated with a campaign originated, under the column heading "Source" 1520. The sources may include one or more of the subjects 100 in example FIG. 1. As an example, the campaign "Internet Usage History" 1510 may include a customer's IP address or MAC address. For the example campaign "Employee Reference Checks", the source may be a particular employee. In example embodiments, clicking on (i.e., selecting) the column heading Source 1520 may result in the campaigns being sorted by source.

The inventory page 1500 of FIG. 15 may also list the "destination" of the personal data associated with a particular campaign under the column heading Destination 1525. Personal data may be stored in any of a variety of places, for example on one or more storage devices 280 that are maintained by a particular entity at a particular location. Different custodians may maintain one or more of the different storage devices. By way of example, referring to FIG. 15, the personal data associated with the Internet Usage History campaign 1510 may be stored in a repository located at the Toronto data center, and the repository may be controlled by the organization (e.g., Acme corporation) or another entity, such as a vendor of the organization that has been hired by the organization to analyze the customer's internet usage history. Alternatively, storage may be with a department within the organization (e.g., its marketing department). In example embodiments, clicking on (i.e., selecting) the column heading Destination 1525 may result in the campaigns being sorted by destination.

On the inventory page 1500, the Access heading 1530 may show the number of transfers that the personal data associated with a campaign has undergone. In example embodiments, clicking on (i.e., selecting) the column heading "Access" 1530 may result in the campaigns being sorted by Access.

The column with the heading Audit 1535 shows the status of any privacy audits associated with the campaign. Privacy audits may be pending, in which an audit has been initiated but yet to be completed. The audit column may also show for the associated campaign how many days have passed since a privacy audit was last conducted for that campaign. (e.g., 140 days, 360 days). If no audit for a campaign is currently required, an "OK" or some other type of indication of compliance (e.g., a "thumbs up" indicia) may be displayed for that campaign's audit status. Campaigns may also be sorted based on their privacy audit status by selecting or clicking on the Audit heading 1535.

In example inventory page 1500, an indicator under the heading Risk 1540 may also display an indicator as to the Risk Level associated with the personal data for a particular campaign. As described earlier, a risk assessment may be made for each campaign based on one or more factors that may be obtained by the system. The indicator may, for example, be a numerical score (e.g., Risk Level of the campaign), or, as in the example shown in FIG. 15, it may be arrows that indicate the Overall Risk Assessment for the campaign. The arrows may be of different shades, or different colors (e.g., red arrows indicating "high risk" campaigns, yellow arrows indicating "medium risk" campaigns, and green arrows indicating "low risk" campaigns). The direction of the arrows—for example, pointing upward or downward, may also provide a quick indication of Overall Risk Assessment for users viewing the inventory page 1500. Each campaign may be sorted based on the Risk Level associated with the campaign.

The example inventory page 1500 may comprise a filter tool, indicated by Filters 1545, to display only the campaigns having certain information associated with them. For example, as shown in FIG. 15, under Collection Purpose 1550, checking the boxes "Commercial Relations," "Provide Products/Services", "Understand Needs," "Develop Business & Ops," and "Legal Requirement" will result the display under the Data Flow Summary 1505 of only the campaigns that meet those selected collection purpose requirements.

From example inventory page 1500, a user may also add a campaign by selecting (i.e., clicking on) Add Data Flow 1555. Once this selection has been made, the system initiates a routine to guide the user in a phase-by-phase manner through the process of creating a new campaign (further details herein). An example of the multi-phase GUIs in which campaign data associated with the added privacy campaign may be input and associated with the privacy campaign record is described in FIG. 8-13 above.

From the example inventory page 1500, a user may view the information associated with each campaign in more depth, or edit the information associated with each campaign. To do this, the user may, for example, click on or select the name of the campaign (i.e., click on Internet Usage History 1510). As another example, the user may select a button displayed on screen indicating that the campaign data is editable (e.g., edit button 1560).

I: FIG. 16: Campaign Information Page and Data Flow Diagram

FIG. 16 shows an example of information associated with each campaign being displayed in a campaign information page 1600. Campaign information page 1600 may be accessed by selecting (i.e., clicking on), for example, the edit button 1560. In this example, Personal Data Collected section 1605 displays the type of personal data collected from the customer for the campaign Internet Usage History. The type of personal data, which may be stored as data elements associated with the Internet Usage History campaign digital record entry. The type of information may include, for example, the customer's Subscriber ID, which may be assigned by the organization (e.g., a customer identification number, customer account number). The type of information may also include data associated with a customer's premises equipment, such as an IP Address, MAC Address, URL History (i.e., websites visited), and Data Consumption (i.e., the number of megabytes or gigabytes that the user has download).

Still referring to FIG. 16, the "About this Data Flow" section 1610 displays relevant information concerning the campaign, such as the purpose of the campaign. In this example, a user may see that the Internet Usage History campaign is involved with the tracking of internet usage from customers in order to bill appropriately, manage against quotas, and run analytics. The user may also see that the business group that is using the sensitive information associated with this campaign is the Internet group. A user may further see that the next privacy audit is scheduled for Jun. 10, 2016, and that the last update of the campaign entry was Jan. 2, 2015. The user may also select the "view history" hyperlink to display the history of the campaign.

FIG. 16 also depicts an example of a Data Flow Diagram 1615 generated by the system, based on information provided for the campaign. The Data Flow Diagram 1615 may provide the user with a large amount of information regarding a particular campaign in a single compact visual. In this example, for the campaign Internet Usage History, the user may see that the source of the personal data is the organization's customers. In example embodiments, as illustrated, hovering the cursor (e.g., using a touchpad, or a mouse) over the term "Customers" may cause the system to display the type of sensitive information obtained from the respective consumers, which may correspond with the information displayed in the "Personal Data Collected" section 1605.

In various embodiments, the Data Flow Diagram 1615 also displays the destination of the data collected from the User (in this example, an Internet Usage Database), along with associated parameters related to backup and deletion. The Data Flow Diagram 1615 may also display to the user which department(s) and what system(s) have access to the personal data associated with the campaign. In this example, the Customer Support Department has access to the data, and the Billing System may retrieve data from the Internet Usage Database to carry out that system's operations. In the Data Flow Diagram 1615, one or more security indicators may also be displayed. The may include, for example, an "eye" icon to indicate that the data is confidential, a "lock" icon to indicate that the data, and/or a particular flow of data, is encrypted, or an "unlocked lock" icon to indicate that the data, and/or a particular flow of data, is not encrypted. In the example shown in FIG. 16, the dotted arrow lines generally depict respective flows of data and the locked or unlocked lock symbols indicate whether those data flows are encrypted or unencrypted.

Campaign information page 1600 may also facilitate communications among the various personnel administrating the campaign and the personal data associated with it. Collaborators may be added through the Collaborators button 1625. The system may draw information from, for example, an active directory system, to access the contact information of collaborators.

If comment 1630 is selected, a real-time communication session (e.g., an instant messaging session) among all (or some) of the collaborators may be instantiated and overlaid on top of the page 1600. This may be helpful, for example, in facilitating population of a particular page of data by multiple users. In example embodiments, the Collaborators 1625 and Comments 1630 button may be included on any graphical user interface described herein, including dialog boxes in which information is entered or selected. Likewise, any instant messaging session may be overlaid on top of a webpage or dialog box. The system may also use the contact information to send one or more users associated with the campaign periodic updates, or reminders. For example, if the deadline to finish entering the campaign data associated with a campaign is upcoming in three days, the business representative of that assigned campaign may be sent a message reminding him or her that the deadline is in three days.

Like inventory page 1500, campaign information page 1600 also allows for campaigns to be sorted based on risk (e.g., Sort by Risk 1635). Thus, for example, a user is able to look at the information for campaigns with the highest risk assessment.

J: FIG. 17: Edit Campaign Dialog

FIG. 17 depicts an example of a dialog box—the edit campaign dialog 1000. The edit campaign dialog 1000 may have editable fields associated with a campaign. In this example, the information associated with the Internet Usage History campaign 310 may be edited via this dialog. This includes the ability for the user to change the name of the campaign, the campaign's description, the business group, the current owner of the campaign, and the particular personal data that is associated with the campaign (e.g., IP address, billing address, credit score, etc.). In example embodiments, the edit campaign dialog 1000 may also allow for the addition of more factors, checkboxes, users, etc.

The system 100 also includes a Historical Record Keeping Module, wherein every answer, change to answer, as well as assignment/re-assignment of owners and collaborators is logged for historical record keeping.

Although embodiments above are described in reference to various systems and methods for creating and managing data flows related to individual privacy campaigns, it should be understood that various aspects of the system described above may be applicable to other privacy-related systems, or to other types of systems, in general. For example, the functionality described above for obtaining the answers to various questions (e.g., assigning individual questions or sections of questions to multiple different users, facilitating collaboration between the users as they complete the questions, automatically reminding users to complete their assigned questions, and other aspects of the systems and methods described above) may be used within the context of Privacy Impact Assessments (e.g., in having users answer certain questions to determine whether a certain project complies with an organization's privacy policies).

While this specification contains many specific embodiment details, these should not be construed as limitations on the scope of any invention or of what may be claimed, but rather as descriptions of features that may be specific to particular embodiments of particular inventions. Certain features that are described in this specification in the context of separate embodiments may also be implemented in combination in a single embodiment. Conversely, various features that are described in the context of a single embodiment may also be implemented in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products.

Many modifications and other embodiments of the invention will come to mind to one skilled in the art to which this invention pertains having the benefit of the teachings presented in the foregoing descriptions and the associated drawings. While examples discussed above cover the use of various embodiments in the context of operationalizing privacy compliance and assessing risk of privacy campaigns, various embodiments may be used in any other suitable context. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for the purposes of limitation.

What is claimed is:

1. A computer-implemented data processing method for determining a privacy audit schedule for a privacy campaign, the data processing method comprising:

displaying, by one or more computer processors, on a graphical user interface, a prompt to create an electronic record for the privacy campaign, wherein the privacy campaign utilizes personal data collected from at least one or more persons or one or more entities;

receiving, by one or more computer processors, a command to create an electronic record for the privacy campaign;

creating, by one or more computer processors, an electronic record for the privacy campaign and digitally storing the record;

presenting, by one or more computer processors, on one or more graphical user interfaces, a plurality of prompts for the input of campaign data related to the privacy campaign;

electronically receiving, by one or more computer processors, campaign data input by one or more users, wherein the campaign data comprises each of:

a description of the campaign;

an identification of one or more types of particular personal data obtained as part of the campaign;

at least one data subject from which the particular personal data was collected;

one or more storage locations where the personal data is to be stored; and data indicating who will have access to the particular personal data;

processing, by one or more computer processors, the campaign data by electronically associating the campaign data with the record for the privacy campaign;

digitally storing, by one or more computer processors, the campaign data in association with the electronic record for the privacy campaign;

determining, by one or more computer processors, based at least in part on the received campaign data, a risk value associated with the privacy campaign, wherein determining the risk value comprises, electronically retrieving, from a data structure, the campaign data associated with the record for the privacy campaign, electronically determining a weighting factor for each of a plurality of risk factors, wherein the plurality of risk factors comprises:

a nature of the particular personal data associated with the campaign;

a physical location of the particular personal data associated with the campaign;

a length of time that the particular personal data associated with the campaign will be retained in storage; and a country of residence of at least one subject from which the particular personal data was collected;

electronically determining a relative risk rating for each of the plurality of risk factors;

electronically calculating a risk value for the privacy campaign based upon, for each respective one of the plurality of risk factors, the relative risk rating for the respective risk factor and the weighting factor for the respective risk factor; and electronically assigning, by one or more computer processors, a privacy audit schedule to the privacy campaign based on the determined risk value for the privacy campaign.

2. The computer-implemented data processing method of claim 1, wherein the risk value for the campaign is a numerical risk value for the campaign.

3. The computer-implemented data processing method of claim 1, wherein the risk value for the campaign is a risk level for the campaign.

4. The computer-implemented data processing method of claim 1, wherein the audit schedule is a default audit schedule that has been predetermined for the risk value associated with the campaign.

5. The computer-implemented data processing method of claim 4, wherein the default audit schedule has been determined based on one or more privacy laws.

6. The computer-implemented data processing method of claim 4, wherein the default audit schedule is modifiable by one or more users.

7. The computer-implemented data processing method of claim 1, further comprising:

receiving, by one or more computer processors, a request to modify the audit schedule assigned to the campaign; and in response to receiving the request, determining, by one or more computer processors, whether the privacy audit schedule assigned to the privacy campaign is modifiable.

8. The computer-implemented data processing method of claim 7, further comprising:

in response to determining that the audit schedule is modifiable, modifying, by one or more computer processors, the privacy audit schedule for the campaign.

9. The computer-implemented data processing method of claim 8, further comprising:

in response to determining that the privacy audit schedule is not modifiable, electronically displaying an indication that the privacy audit schedule is not modifiable.

10. The computer-implemented data processing method of claim 1, further comprising:

determining whether a privacy audit, to be performed according to the privacy audit schedule, is to be performed within a threshold period of time from a current time; and in response to determining that the privacy audit is to be performed within the threshold period of time from the current time, generating an electronic alert indicating that the privacy audit is to be performed within the threshold period of time from the current time.

11. The computer-implemented data processing method of claim 1, further comprising:

receiving an electronic confirmation that a scheduled privacy audit, made according to the privacy audit schedule, has been completed; and in response to receiving the electronic confirmation, updating the audit schedule to reflect that the scheduled privacy audit has been completed.

12. The computer-implemented data processing method of claim 11, wherein the electronic confirmation received is based upon an electronic verification generated if all portions of the scheduled privacy audit have been verified as completed by one or more users.

13. The computer-implemented data processing method of claim 12, wherein the method further comprises:

receiving documentation related to the compliance of the privacy campaign;

electronically associating the documentation received with the record for the campaign; and digitally storing the documentation in association with the record for the campaign in an electronic storage device.

14. The computer-implemented data processing method of claim 1, wherein the method further comprises:

determining whether the scheduled privacy audit is overdue based on whether an electronic confirmation that a scheduled privacy audit, made according to the privacy audit schedule, has been completed; and in response to determining that the privacy audit is overdue, generating an electronic alert indicating that the privacy audit is overdue.

15. The method of claim 1, wherein the method further comprises:

electronically retrieving the campaign record and the campaign data associated with the record; and generating, for display, a computer-generated user interface comprising an inventory page, wherein the inventory page comprises a list of a plurality of campaigns and audit information for one or more of the plurality of campaigns.

16. The computer-implemented data processing method of claim 1, wherein the plurality of risk factors further comprises a number of individuals having access to the particular personal data associated with the campaign.

17. The computer-implemented data processing method of claim 1, wherein the plurality of risk factors further comprises a type of individual from which the particular personal data associated with the campaign originated.

18. The computer-implemented data processing method of claim 1, wherein the step of determining a weighting factor for each of a plurality of risk factors comprises using one or more user customizations to determine at least one weighting factor for a respective one of the plurality of risk factors.

19. A computer-implemented data processing method for determining a privacy audit schedule for a privacy campaign, the data processing method comprising:
- receiving, by one or more computer processors, a command to set up the privacy campaign in privacy management software;
- in response to receiving the command, creating, by one or more computer processors, an electronic record for the privacy campaign and digitally storing the record;
- communicating, by one or more computer processors, to one or more users, a plurality of prompts for the input of campaign data related to the privacy campaign;
- electronically receiving, by one or more computer processors, campaign data input by one or more users, wherein the campaign data comprises: (1) data indicating what types of particular personal data are obtained as part of the privacy campaign; and (2) data indicating who will have access to the particular personal data;
- processing, by one or more computer processors, the campaign data by electronically associating the campaign data with the record for the privacy campaign;
- digitally storing, by one or more computer processors, the campaign data in association with the record for the privacy campaign;
- determining, by one or more computer processors, based at least in part on the received campaign data, a risk value associated with the privacy campaign, wherein determining the risk value comprises:
- electronically retrieving, from a data structure, the campaign data associated with the record for the privacy campaign,
- electronically determining a weighting factor for each of a plurality of risk factors, wherein the plurality of risk factors comprises:
  - a nature of the particular personal data associated with the campaign;
  - a physical location of the particular personal data associated with the campaign;
  - a length of time that the particular personal data associated with the campaign will be retained in storage; and
  - a country of residence of at least one subject from which the particular personal data was collected;
- electronically determining a relative risk rating for each of the plurality of risk factors;
- electronically calculating a risk value for the privacy campaign based upon, for each respective one of the plurality of risk factors, the relative risk rating for the respective risk factor and the weighting factor for the respective risk factor; and
- electronically assigning, by one or more computer processors, a privacy audit schedule to the privacy campaign based on the determined risk value for the privacy campaign.

20. The computer-implemented data processing method of claim 19, wherein the risk value for the campaign is a risk level for the campaign.

21. The computer-implemented data processing method of claim 20, wherein the audit schedule is a default audit schedule that has been predetermined for the risk level associated with the campaign.

22. The computer-implemented data processing method of claim 19, wherein the campaign data comprises data indicating whether personal data from one or more minors is obtained as part of the privacy campaign.

23. The computer-implemented data processing method of claim 19, wherein, the campaign data comprises a description of the campaign, and
the description of the campaign comprises a name of the campaign.

24. The computer-implemented data processing method of claim 19, wherein the campaign data comprises one or more storage locations for the personal data.

25. The computer-implemented data processing method of claim 19, wherein the plurality of risk factors further comprises a number of individuals having access to the particular personal data associated with the campaign.

26. The computer-implemented data processing method of claim 17, wherein the plurality of risk factors further comprises a type of individual from which the particular personal data associated with the campaign originated.

27. The computer-implemented data processing method of claim 19, wherein the plurality of risk factors further comprises a type of individual from which the particular personal data associated with the campaign originated.

28. A computer-implemented data processing method for determining a privacy audit schedule for a privacy campaign, the data processing method comprising:
- receiving, by one or more computer processors, a command to set up privacy campaign in privacy management software;
- in response to receiving the command, creating, by one or more computer processors, an electronic record for the privacy campaign and digitally storing the record;
- communicating, by one or more computer processors, to one or more users, a plurality of prompts for the input of campaign data related to the privacy campaign;
- electronically receiving, by one or more computer processors, campaign data input by one or more users, wherein the campaign data comprises: (1) data indicating what types of information are obtained as part of the privacy campaign; and (2) data indicating one or more storage locations for the personal data;
- processing, by one or more computer processors, the campaign data by electronically associating the campaign data with the record for the privacy campaign;
- digitally storing, by one or more computer processors, the campaign data in association with the record for the privacy campaign;
- determining, by one or more computer processors, based at least in part on the received campaign data, a risk value associated with the privacy campaign, wherein determining the risk value comprises,
  - electronically retrieving, from a data structure, the campaign data associated with the record for the privacy campaign,
  - electronically determining a weighting factor for each of a plurality of risk factors, wherein the plurality of risk factors comprises:
    - a nature of the particular personal data associated with the campaign;
    - a physical location of the particular personal data associated with the campaign;
    - a length of time that the particular personal data associated with the campaign will be retained in storage; and
    - a country of residence of at least one subject from which the particular personal data was collected;
  - electronically determining a relative risk rating for each of the plurality of risk factors;
  - electronically calculating a risk value for the privacy campaign based upon, for each respective one of the plurality of risk factors, the relative risk rating for the respective risk factor and the weighting factor for the respective risk factor; and electronically assigning, by one or more computer processors, a privacy audit schedule to the privacy campaign based on the determined risk value for the privacy campaign.

29. The computer-implemented data processing method of claim 28, wherein the campaign data comprises a description of the campaign.

30. The computer-implemented data processing method of claim 28, further comprising:

receiving an electronic confirmation that a scheduled privacy audit, made according to the privacy audit schedule, has been completed; and in response to receiving the electronic confirmation, updating the audit schedule to indicate that the privacy campaign should be audited again by a predetermined date in the future.

* * * * *

UNITED STATES PATENT AND TRADEMARK OFFICE
CERTIFICATE OF CORRECTION

PATENT NO. : 9,892,477 B2
APPLICATION NO. : 15/633703
DATED : February 13, 2018
INVENTOR(S) : Kabir A. Barday Page 1 of 1

It is certified that error appears in the above-identified patent and that said Letters Patent is hereby corrected as shown below:

In the Claims

At Claim 1, Column 34, Line 60, before the words "personal data" insert the word -- particular --

At Claim 19, Column 37, Line 31, replace the word "campaign," with the word -- campaign; --

At Claim 23, Column 37, Line 67, replace the word "wherein," with the word -- wherein: --

At Claim 23, Column 38, Line 1, replace the word "campaign," with the word -- campaign; --

At Claim 28, Column 38, Line 24, before the words "privacy campaign" insert the word -- the --

At Claim 28, Column 38, Line 47, replace the word "comprises," with the word -- comprises: --

At Claim 28, Column 38, Line 50, replace the word "campaign," with the word -- campaign; --

At Claim 28, Column 38, Line 54, remove the word "particular"

At Claim 28, Column 38, Line 56, remove the word "particular"

At Claim 28, Column 38, Line 58, remove the word "particular"

At Claim 28, Column 38, Line 62, remove the word "particular"

Signed and Sealed this
Twenty-first Day of August, 2018

Andrei Iancu
*Director of the United States Patent and Trademark Office*